US007520613B2

(12) United States Patent
Saito et al.

(10) Patent No.: US 7,520,613 B2
(45) Date of Patent: Apr. 21, 2009

(54) WAVEFRONT ABERRATION COMPENSATING APPARATUS AND OPHTHALMOLOGIC UNIT HAVING THE SAME

(75) Inventors: Noriko Saito, Tokyo (JP); Akio Kobayashi, Tokyo (JP); Hiroyuki Kawashima, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 0 days.

(21) Appl. No.: 12/047,946

(22) Filed: Mar. 13, 2008

(65) Prior Publication Data

US 2008/0225228 A1    Sep. 18, 2008

(30) Foreign Application Priority Data

Mar. 14, 2007    (JP)    ............................. 2007-065524

(51) Int. Cl.
*A61B 3/10*    (2006.01)
*A61B 3/14*    (2006.01)
(52) U.S. Cl. ...................................... 351/205; 351/206
(58) Field of Classification Search ................ 351/205, 351/206, 210, 246
See application file for complete search history.

(56) References Cited

U.S. PATENT DOCUMENTS 7,448,752 B2 * 11/2008 Levine ........................ 351/205

FOREIGN PATENT DOCUMENTS

JP          2005-224328          8/2005

OTHER PUBLICATIONS

U.S. Appl. No. 12/048,095, Noriko Saito et al.
U.S. Appl. No. 12/048,024, Noriko Saito et al.

* cited by examiner

*Primary Examiner*—William C Choi
*Assistant Examiner*—Jack Dinh
(74) *Attorney, Agent, or Firm*—Dickstein Shapiro LLP

(57)    ABSTRACT

A wavefront aberration compensating apparatus, including: a deformable mirror which compensates a wavefront aberration of a light flux and includes electrodes, and a thin-film mirror which changes a configuration thereof in accordance with a voltage value applied to each of the electrodes; an optical system provided with the deformable mirror and including an object subjected to aberration compensation; a wavefront sensor which measures the wavefront aberration of the light flux; a memory which stores therein a voltage template provided for each expansion mode according to a polynomial of wavefront aberration, as a voltage alignment data for the electrodes which induces the corresponding expansion mode; and a controller configured to determine a superposition amplitude value of each of the expansion modes and calculate the voltage value applied to each of the electrodes by using the voltage templates stored such that the wavefront aberration obtained by the wavefront sensor becomes a desired aberration, and to repeat compensation of the configuration of the thin-film mirror on the basis of the calculated voltage value, such that the wavefront aberration of the light flux measured by the wavefront sensor is suppressed.

15 Claims, 9 Drawing Sheets

WAVEFRONT ABERRATION COMPENSATING APPARATUS AND OPHTHALMOLOGIC UNIT HAVING THE SAME

CROSS REFERENCE TO RELATED APPLICATIONS

The present application is based on and claims priority from Japanese Patent Application No. 2007-065524, filed Mar. 14, 2007, the disclosure of which is hereby incorporated by reference herein in its entirety.

BACKGROUND

The present invention relates to an apparatus for compensating a wavefront aberration. More specifically, the invention relates to a wavefront aberration compensating apparatus for performing an aberration compensation which suppresses a wavefront aberration, as a factor for determining sharpness of an image when an object subjected to the aberration compensation, such as an eye for example, is observed, photographed and so forth at high magnification, to be small, and relates to an ophthalmologic unit having the same.

Conventionally, there is known a retinal camera which performs observation and photographing of a retina, by imaging the retina on the basis of a reflected light flux from the illuminated retina. However, since the reflected light flux from the retina passes through an ocular optical system including a cornea, a crystalline lens, a vitreous body for example, the retinal camera of this kind cannot obtain an image of the retina at high resolution, due to an influence of an aberration in the ocular optical system. Therefore, the conventional retinal camera has a problem in that a sharp image of the retina cannot be obtained, even attempting to perform observation, photographing and so forth of the retina at high magnification. Incidentally, the ocular optical system is far from an ideal optical element, possesses optical refractive properties which generate various aberrations such as myopia and astigmatism, and a wavefront due to the reflected light flux from the retina has distortions.

On the other hand, for example, Japanese patent application publication No. 2005-224328 proposes an apparatus capable of obtaining a sharp image of a retina even when a magnification is increased. The apparatus disclosed in JP2005-224328A is provided with an aberration measurement part which measures an optical aberration of an eye, and an aberration compensation part including a deformable mirror for compensating distortions of the wavefront of the reflected light flux caused by the optical aberration of the eye on the basis of a signal supplied from the aberration measurement part.

In a conventional technology, plural kinds of voltage variation templates such as a concentric template, a symmetrical template and an asymmetrical template are provided for adjusting a deformable mirror when a wavefront aberration is to be compensated by using the deformable mirror. The voltage variation templates are selected on the basis of the measured wavefront aberration, and one of voltage patterns as voltage values for respective electrodes is determined from the selected voltage variation template. The determination of the voltage patterns is repeated to perform the compensation of the wavefront aberration in which the deformable mirror is used.

Generally, an arithmetic processing method for the compensation of the wavefront aberration, in which the templates are utilized, includes a distortion, generated when a voltage is applied to a single electrode, as an influence function. The influence functions corresponding to the respective electrodes are superposed to calculate voltage alignment data corresponding to an objective configuration of the deformable mirror. Hence, since a unit of the templates is equivalent to the number of electrodes, an amount of calculation increases depending upon the number of electrodes.

Additionally, in the conventional technology in which three kinds of templates are provided, a congruence of the wavefront aberration to each expansion mode subjected to the compensation cannot be obtained by the templates of three kinds. Also, it is necessary to use the arithmetic processing method for the wavefront aberration compensation, in which the distortion generated when the voltage is applied to the predetermined electrode is included as the influence function, and to calculate a superposition coefficient used when the influence functions corresponding to the respective electrodes are superposed. The calculation for the superposition coefficients, however, requires time. Therefore, it is often said that the arithmetic processing method for the compensation of the wavefront aberration, in which the templates are used, is normally not suitable for the deformable mirror having the large number of electrodes.

Furthermore, the number of times of repetition of the compensation by the voltage patterns decreases when a target value for a residual aberration, as a difference between a wavefront aberration of an eye for example and an aberration compensated by the deformable mirror, is set to be large. Thus, the time required, for example, in photographing of a retina from initiation of the photographing to finishing of the photographing is shortened. However, a sharp image cannot be photographed when a high magnification is set.

In contrast, the sharp image is obtainable even when the high magnification is set, when the target value for the residual aberration is set to be small. However, the number of times for the repeated compensation by the voltage patterns is increased, and thus, the time required, for example, in the photographing of the retina from the initiation of the photographing to the finishing of the photographing becomes long.

Here, reasons why the control of compensating the deformable mirror is repeatedly performed by the voltage patterns, such that a shape of a thin-film mirror of the deformable mirror becomes nearer to the objective configuration, will be described.

The deformable mirror includes plural electrodes arranged at a predetermined interval on a back face of the thin-film mirror, and a voltage is applied to each of the electrodes, to deform the thin-film mirror only by a pulling force or an electrostatic force. In addition, since the thin-film mirror of the deformable mirror is a continuum, the respective electrodes cannot be treated individually for the shape deformation of the thin-film mirror. Hence, when one point of the thin-film mirror is pulled by one electrode, a part of the thin-film mirror corresponding to that one electrode is deformed largely, and at the same time, a part of the thin-film mirror corresponding to other electrodes is also deformed. Therefore, the compensation control of the deformable mirror is performed repeatedly by the voltage patterns, since the entire surface of the mirror is influenced when one part of the thin-film mirror is pulled.

Secondly, when a retina of an eye is to be photographed for example, a duration time in which a person can keep its eye open with good condition is several seconds for a person of shorter duration time, although such a duration time varies depending upon individuals. Thus, in order to complete a procedure from the initiation of the compensation of the wavefront aberration to the photographing within seconds, it is important that an optical system reach the aimed wavefront aberration with the minimum possible number of times of the compensation.

Additionally, in a field of photographing a retina of an eye for example, there has been a demand for photographing a sharp image at a high-magnification, such that a confirmation is possible to the extent of a visual cell of the retina, in order to increase accuracy in examination. To meet this demand, since the magnification can be made higher while sharpness of the image is maintained as the residual aberration becomes smaller, it is necessary to improve a limit of the aberration compensation by using the deformable mirror in which the number of electrodes, to which a voltage is applied, is large.

Therefore, in the compensation control of the deformable mirror, how to anticipate the voltage patterns for generating a configuration to compensate the wavefront aberration remains as a problem which still cannot be solved, in order for the optical system to reach the aimed wavefront aberration with the minimum possible number of times of the compensation from data on a shape of the aberration measured by a wavefront sensor, even when the deformable mirror having the large number of electrodes is used.

SUMMARY

At least one objective of the present invention is to provide a wavefront aberration compensating apparatus and an ophthalmologic unit having the same, capable of accomplishing compensation which suppresses a residual aberration to be small with good responsiveness at a short time, and of obtaining an extremely sharp image even if high-magnification is set, even when a deformable mirror having the large number of electrodes to which a voltage is applied is used for compensation of a wavefront aberration.

To achieve these and other advantages and in accordance with the purpose of the invention, as embodied and broadly described herein, the invention provides a wavefront aberration compensating apparatus, comprising: a deformable mirror which compensates a wavefront aberration of a light flux entered, the deformable mirror including a plurality of electrodes, and a thin-film mirror which changes a configuration thereof in accordance with a voltage value applied to each of the electrodes; an optical system provided with the deformable mirror, and including an object subjected to aberration compensation; a wavefront sensor which receives the light flux traveled through the object and the deformable mirror, and which measures the wavefront aberration of the light flux; a memory which stores therein a voltage template provided for each expansion mode according to a polynomial of wavefront aberration, as a voltage alignment data for the electrodes which induces the corresponding expansion mode of the expansion modes; and a controller configured to determine a superposition amplitude value of each of the expansion modes and calculate the voltage value applied to each of the electrodes by using the voltage templates stored in the memory, such that the wavefront aberration obtained by the wavefront sensor becomes a desired aberration, and to repeat compensation of the configuration of the thin-film mirror of the deformable mirror on the basis of the calculated voltage value, such that the wavefront aberration of the light flux measured by the wavefront sensor is suppressed.

Advantageously, the controller is configured to: apply an initial voltage to each of the electrodes such that an displacement amount of the thin-film mirror becomes an initial displacement amount; and control the configuration of the thin-film mirror created according to a voltage pattern generated for the electrodes to be a configuration which negates a configuration of the wavefront aberration of the light flux entered through the object, such that the wavefront aberration included in the light flux after reflection from the deformable mirror is suppressed to be small.

Advantageously, the wavefront sensor comprises: a Hartmann plate in which micro-lenses are aligned in a lattice-like configuration; and a two-dimensional charge-coupled device, and wherein the wavefront sensor measures the wavefront aberration of the object by: dividing light reflected from the object according to projection of a point light source onto the object and traveled through the object and the deformable mirror into plural light fluxes by the Hartmann plate; measuring point-image positions of the respective light fluxes by the two-dimensional charge-coupled device; and comparing the measured point-image positions with point-image positions according to an ideal object in which the aberration compensation is unnecessary.

Advantageously, the memory stores therein the voltage template provided for each of the expansion modes according to Zernike polynomials of the wavefront aberration, as the voltage alignment data for the electrodes which induces the corresponding expansion mode of the expansion modes subjected to the compensation.

Advantageously, the controller is configured to: load an amplitude value in each of the expansion modes from expansion data according to Zernike polynomials of a residual aberration which is after the compensation of the wavefront aberration; load the voltage value applied to each of the electrodes as a previous voltage value used in a previous compensation of the wavefront aberration; load the stored voltage templates inducing the corresponding expansion modes; calculate objective Zernike polynomial data of the deformable mirror; load previously calculated a line-column in which wavefront configuration data corresponding to the respective voltage templates are aligned; calculate a superposition coefficient obtained from the calculated objective Zernike polynomial data and the loaded line-column as the superposition amplitude value of each of the expansion modes; and calculate the voltage value applied to each of the electrodes in a current compensation, by the voltage templates, the calculated superposition coefficient as the superposition amplitude value, the previous voltage value, and a feedback gain.

Advantageously, the controller is configured to: load an amplitude value in each of the expansion modes from expansion data according to Zernike polynomials of a residual aberration which is after the compensation of the wavefront aberration; load the voltage value applied to each of the electrodes as a previous voltage value used in a previous compensation of the wavefront aberration; load the stored voltage templates inducing the corresponding expansion modes; calculate a ratio of wavefront configuration data corresponding to the respective voltage templates to wavefront configuration data of the respective expansion modes as the superposition amplitude value of each of the expansion modes; and calculate the voltage value applied to each of the electrodes, by the voltage templates, the calculated ratio as the superposition amplitude value, the previous voltage value, and a feedback gain.

Advantageously, the controller is configured to: load an amplitude value in each of the expansion modes from expansion data according to Zernike polynomials of a residual aberration which is after the compensation of the wavefront aberration; load the voltage value applied to each of the electrodes as a previous voltage value used in a previous compensation of the wavefront aberration; load the stored voltage templates inducing the corresponding expansion modes; calculate a value obtained by reversing plus and minus signs of the amplitude value in each of the expansion modes as the superposition amplitude value of each of the expansion modes; and calculate the voltage value applied to each of the electrodes, by the voltage templates, the calculated value as the superposition amplitude value, the previous voltage value, and a feedback gain.

Advantageously, the controller is configured to repeat the compensation of the configuration of the thin-film mirror of the deformable mirror, until a residual aberration after the compensation of the wavefront aberration becomes equal to or less than a target value determined on the basis of an allowable wavefront aberration in which a sharp image at the time when at least one of observation and photographing of the object is obtained by a set magnification.

Advantageously, the object comprises an eye, and wherein the controller is configured to: perform compensation of a spherical diopter power component and an astigmatism power component within the wavefront aberration generated due to a flexing characteristic of the eye as a lower order wavefront aberration compensation; and compensate a component of the wavefront aberration remained after the lower order wavefront aberration compensation and a component of the wavefront aberration higher in order than orders subjected to the lower order wavefront aberration compensation by deforming the deformable mirror.

Advantageously, the controller is configured to: adjust the spherical diopter power component within the wavefront aberration by a focusing mechanism of an autofocusing system, on the basis of the measurement of the wavefront aberration by the wavefront sensor; adjust the astigmatism power component within the wavefront aberration by a lens for astigmatism compensation, on the basis of the measurement of the wavefront aberration by the wavefront sensor; and repeat the lower order wavefront aberration compensation by the adjustment of the spherical diopter power component with the focusing mechanism and the adjustment of the astigmatism power component with the lens, until a residual aberration after the compensation of the wavefront aberration becomes equal to or less than a defined value determined on the basis of second order in the expansion modes according to Zernike polynomials.

Advantageously, the controller is configured to: initiate the compensation of the configuration of the thin-film mirror of the deformable mirror after the lower order wavefront aberration compensation is performed; and repeat the compensation of the configuration of the thin-film mirror of the deformable mirror, until a residual aberration after the compensation of the wavefront aberration becomes equal to or less than a target value determined on the basis of orders in the expansion modes by Zernike polynomials, at least to the sixth order.

Advantageously, the controller is configured to perform at least one of observation and photographing of a retina of an eye as the object, when a residual aberration after the wavefront aberration becomes equal to or less than a target value.

In addition, the invention provides a wavefront aberration compensating apparatus, comprising: a deformable mirror which compensates a wavefront aberration of a light flux entered, the deformable mirror including a plurality of electrodes, and a thin-film mirror which changes a configuration thereof in accordance with a voltage value applied to each of the electrodes; an optical system provided with the deformable mirror, and including an object subjected to aberration compensation; a wavefront sensor which receives the light flux traveled through the object and the deformable mirror, and which measures the wavefront aberration of the light flux; voltage template storing means for storing therein a voltage template provided for each expansion mode according to a polynomial of wavefront aberration, as a voltage alignment data for the electrodes which induces the corresponding expansion mode of the expansion modes; voltage calculating means for determining a superposition amplitude value of each of the expansion modes, and calculating the voltage value applied to each of the electrodes by using the voltage templates stored in the voltage template storing means, such that the wavefront aberration obtained by the wavefront sensor becomes a desired aberration; and deformable mirror controlling means for performing a control of repeating compensation of the configuration of the thin-film mirror of the deformable mirror on the basis of the voltage value calculated by the voltage calculating means, such that the wavefront aberration of the light flux measured by the wavefront sensor is suppressed.

Furthermore, the invention provides an ophthalmologic unit, comprising the wavefront aberration compensating apparatus according to any one of the wavefront aberration compensating apparatuses described above.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the specification, serve to explain the principles of the invention.

DETAILED DESCRIPTION

Figure 1:
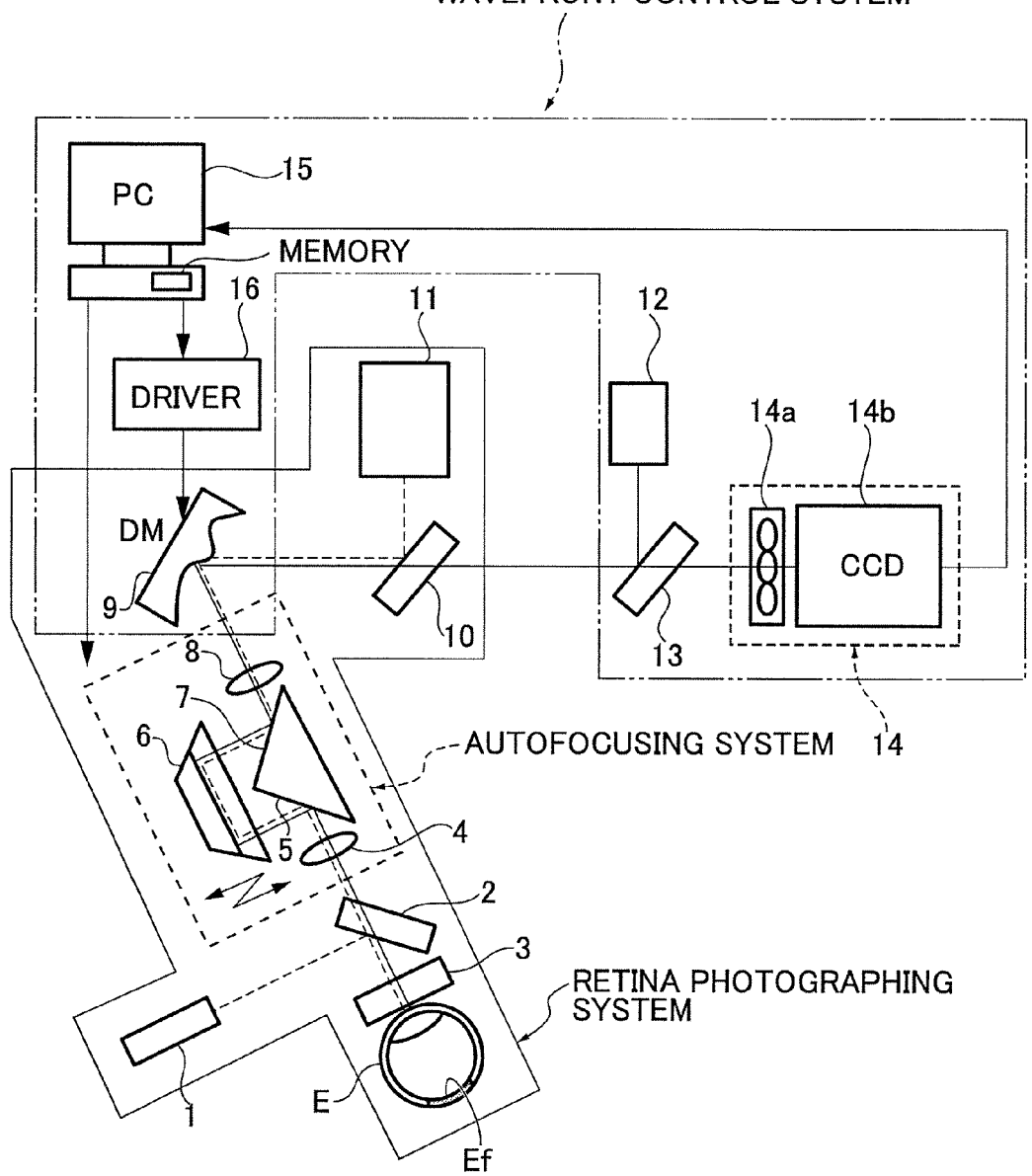
FIG. 1 is an overall view illustrating an ophthalmologic unit applied with a wavefront aberration compensating apparatus according to a first embodiment of the invention.

Reference will now be made in detail to the present preferred embodiments of the invention, examples of which are illustrated in the accompanying drawings. Wherever possible, the same reference numbers are used in the drawings and the description to refer to the same or like parts. The scope of the present invention, however, is not limited to these embodiments. Within the scope of the present invention, any structure and material described below can be appropriately modified.

First Embodiment

First of all, a structure will be described.

FIG. 1 illustrates an ophthalmologic unit applied with a wavefront aberration compensating apparatus according to a first embodiment of the invention. Here, for example, the wavefront aberration compensating apparatus refers to a system realized by having a function of negating a wavefront aberration by a deformable mirror, which may sometimes be called as a compensation optics system or an adaptive optics system.

Referring to FIG. 1, the ophthalmologic unit according to the first embodiment includes a retina photographing system and a wavefront control system. The retina photographing system photographs a retina of an eye, and the wavefront control system compensates a wavefront aberration by using a deformable mirror built in the retina photographing system.

First, the retina photographing system will be described.

The retina photographing system photographs the retina Ef of the eye E. The retina photographing system includes, for example, a semiconductor laser light source 1, a beam splitter 2, a variable cylindrical lens (a lens for astigmatism compensation) 3, a first lens 4, a first mirror 5, a movable prism (focusing mechanism) 6, a second mirror 7, a second lens 8, the deformable mirror 9, a dichroic mirror 10, and a highly-sensitive CCD (Charge-Coupled Device) camera 11.

Semiconductor laser light emitted from the semiconductor laser light source 1 passes through the beam splitter 2 and the variable cylindrical lens 3, which can be set at the arbitrary power of astigmatism, and then enters the eye E to illuminate the retina Ef. In the present embodiment, the semiconductor laser light emitted from the semiconductor laser light source 1 has a wavelength of 633 nm, although it is not limited thereto. The light reflected from the retina Ef as reflected light is subjected to reduction of an influence of the astigmatism with the variable cylindrical lens 3 set according to the power of astigmatism of the eye E. The reflected light then transmits the beam splitter 2, and enters an autofocusing system. The autofocusing system is structured of the first lens 4, the first mirror 5, the movable prism 6, the second mirror 7, and the second lens 8. The movable prism 6 of the autofocusing system is driven in a direction of an arrow illustrated in FIG. 1 corresponding to a spherical diopter power of the eye E to change an optical path length so as to reduce an influence of myopia, hyperopia and so forth. A light flux from the autofocusing system becomes substantially parallel light, which is reflected by the deformable mirror 9. A direction of the reflected parallel light is then changed by the dichroic mirror 10 such that the parallel light is incident on the highly-sensitive CCD camera 11 used for the photographing of the retina. Thereby, the retina is imaged on a coupled device of the highly-sensitive CCD camera 11.

Next, the wavefront control system will be described.

The wavefront control system compensates the wavefront aberration by using the deformable mirror 9 included in the retina photographing system. The wavefront control system includes, for example, a semiconductor laser light source 12, a beam splitter 13, a wavefront sensor 14, a controller 15, and a driver 16. The semiconductor laser light source 12 may be replaced by a SLD (Super Luminescent Diode) light source. In the present embodiment, a personal computer is used as the controller 15, although it is not limited thereto. The controller 15 can be any device as long as a suitable controlling element, such as a CPU (Central Processing Unit), is included. Note that the wavefront control system according to the present embodiment employs a structure in which the deformable mirror 9 of the retina photographing system is shared therewith.

Semiconductor laser light emitted from the semiconductor laser light source 12 is reflected by the beam splitter 13. In the present embodiment, the semiconductor laser light emitted from the semiconductor laser light source 12 has a wavelength of 840 nm, although it is not limited thereto. The reflected semiconductor laser light then passes through the dichroic mirror 10, the deformable mirror 9, the autofocusing system, the beam splitter 2, and the variable cylindrical lens 3 to be incident on the eye E, so as to image the retina Ef. The light reflected from the retina Ef as reflected light passes through the variable cylindrical lens 3, the beam splitter 2, and the autofocusing system, which is then reflected by the deformable mirror 9 in which a configuration thereof is controlled. Thereby, the wavefront aberration is compensated. Thereafter, the reflected light transmits the dichroic mirror 10 and the beam splitter 13 with a state in which the wavefront aberration which has not been compensated completely by the deformable mirror 9 is included, i.e., a state that a residual aberration, in which an aimed aberration is subtracted from the aberration of a light flux reflected from the deformable mirror 9, is included. Then, reflected light, having transmitted the dichroic mirror 10 and the beam splitter 13, is incident on the wavefront sensor 14. The wavefront sensor 14 includes, for example, a Hartmann plate 14a and a two-dimensional CCD (Charge-Coupled Device) 14b. Thereby, information on the wavefront aberration is detected as an image. The CCD image obtained by the two-dimensional CCD 14b is subjected to an image processing by the controller 15, so as to calculate the residual aberration. The controller 15 computes voltage data, used for compensating the configuration of a thin-film mirror of the deformable mirror 9, by utilizing a later-described compensation algorithm, and repeats a compensation processing driven by the driver 16 until the calculated residual aberration becomes equal to or less than a target value.

The wavefront control system is based on a closed-loop, and is controlled such that the residual aberration becomes small. In the present embodiment, the retina Ef is photographed at high magnification by the highly-sensitive CCD camera 11 of the retina photographing system, at the time when the residual aberration is decreased to be equal to or less than the target value.

Now, a structure of the deformable mirror 9 will be described.

Figure 2A:
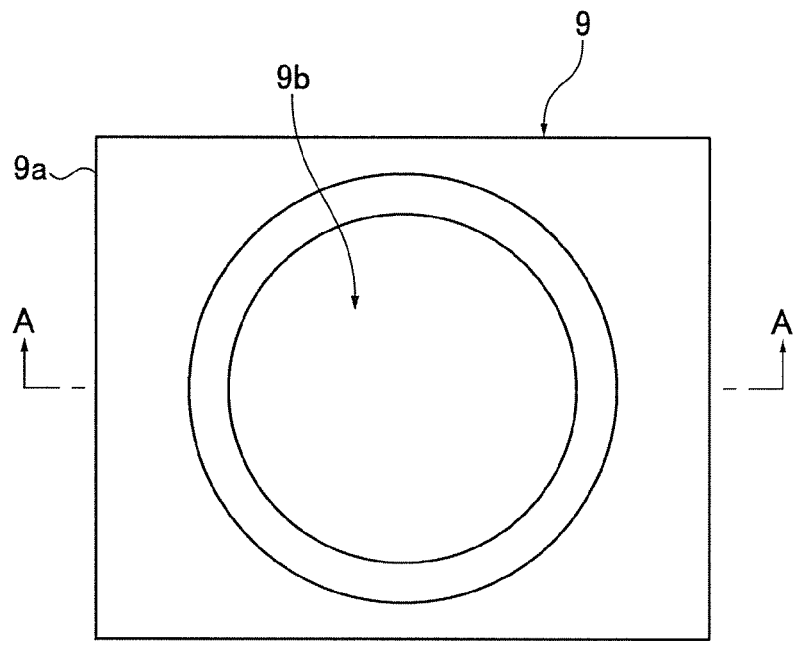
FIG. 2A is a plan view illustrating one example of a deformable mirror shared by a retina photographing system and a wavefront control system according to the first embodiment.
Figure 2B:
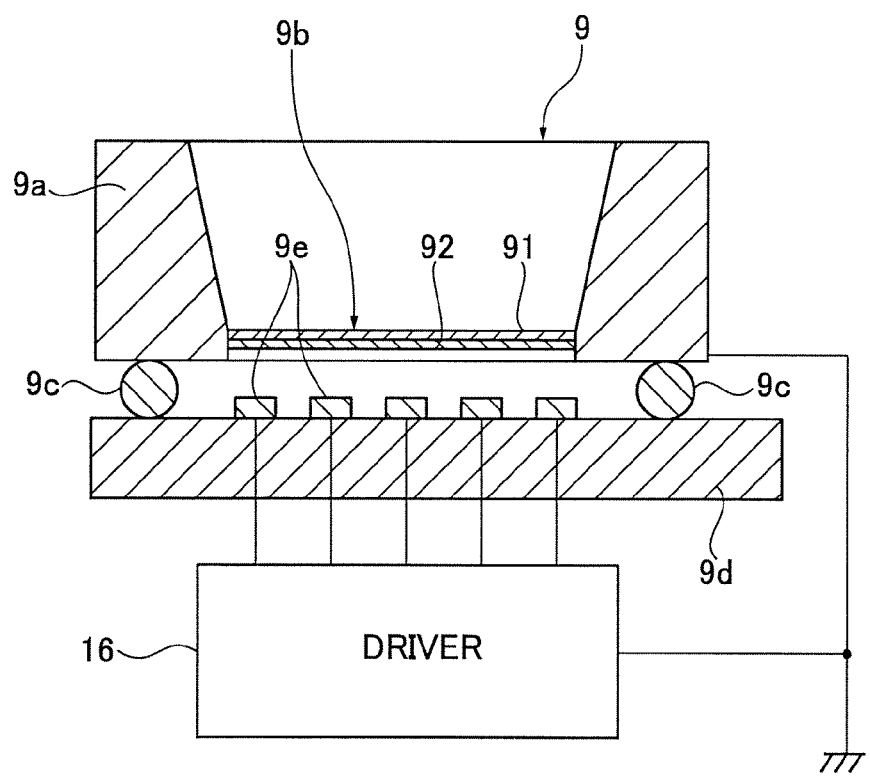
FIG. 2B is a cross-sectional view taken along an A-A line of FIG. 2A.
Figure 3:
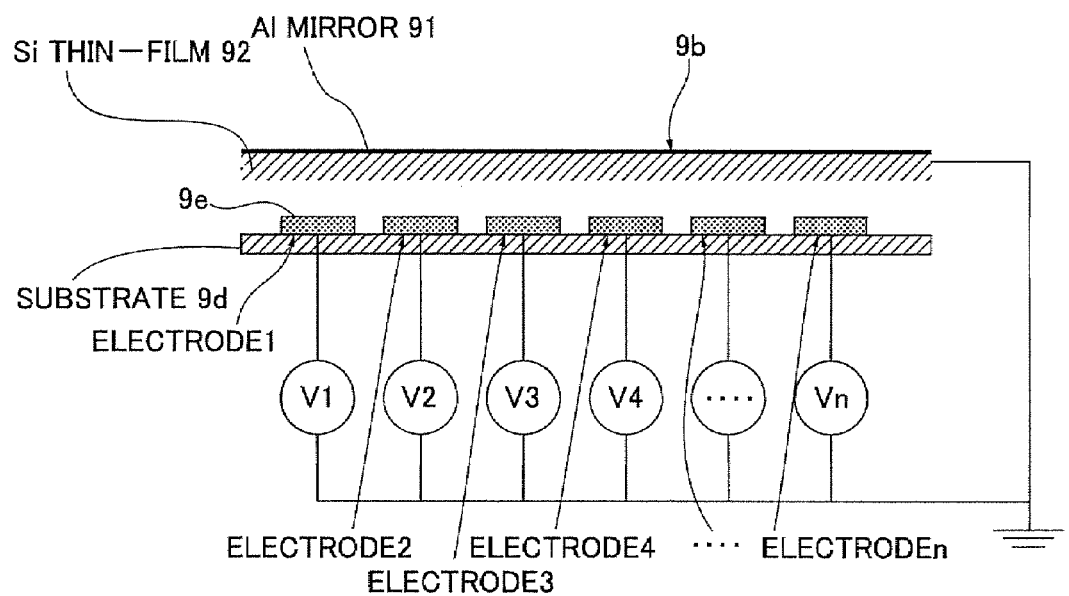
FIG. 3 is a cross-sectional view illustrating a thin-film mirror and electrodes of the deformable mirror.
Figure 4:
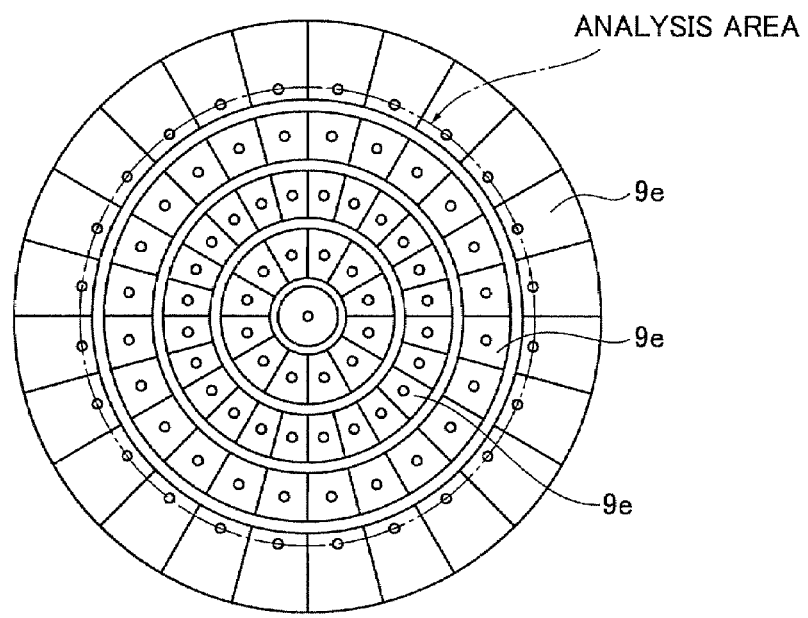
FIG. 4 is a plan view illustrating an example of arrangement of the electrodes of the deformable mirror.

FIG. 2A illustrates one example of the deformable mirror 9 shared by the retina photographing system and the wavefront control system according to the present embodiment. FIG. 2B is a cross-sectional view taken along an A-A line of FIG. 2A. FIG. 3 is a cross-sectional view which illustrates the thin-film mirror and electrodes of the deformable mirror 9. FIG. 4 illustrates an example of arrangement of the electrodes of the deformable mirror 9.

Referring to FIGS. 2A and 2B, the deformable mirror 9 includes, for example, a mirror frame 9a, a thin-film mirror 9b, spacers 9c, an electrode substrate 9d, and electrodes 9e.

Referring to FIG. 3, the thin-film mirror 9b is stretched on the mirror frame 9a, and includes a two-layer structure of a mirror or preferably an aluminum (Al) mirror 91 disposed on an optical path side, and a thin-film or preferably a silicon (Si) thin-film 92 disposed on an electrode side. The mirror 91 is a reflective film, and formed by evaporating a material having high reflectivity on the thin-film 92. The thin-film 92 has flexibility, and has a thickness of about 4 μm, although it is not limited thereto.

Each of the spacers 9c retains a gap length between the thin-film mirror 9b and the electrodes 9e at a predetermined value. In the present embodiment, a ball having high rigidity is used for the spacers 9c, although it is not limited thereto.

Referring to FIG. 4, for example, the plural electrodes 9e are disposed on the electrode substrate 9d, and are divided into 85 electrodes to be aligned concentrically and radially. In FIG. 4, black spots denote application points, and a dashed line denotes an analysis area in which the wavefront is regenerated from wavefront measurement data. In the present embodiment, the analysis area is set in an area connecting the application points located at the outermost circumference of the electrode substrate 9d.

Referring to FIG. 2B, the driver 16 is provided as a circuit for driving the respective electrodes 9e, i.e., an electrode 1 to an electrode "n", individually with voltage. Referring to FIG. 3, electrostatic voltage values $V_1$ to $V_n$ are applied to the respective electrodes 9e, such that the deformation of the thin-film mirror 9b is generated corresponding to each of the electrodes 9e.

Next, a structure of the wavefront sensor 14 will be described.

Figure 5:
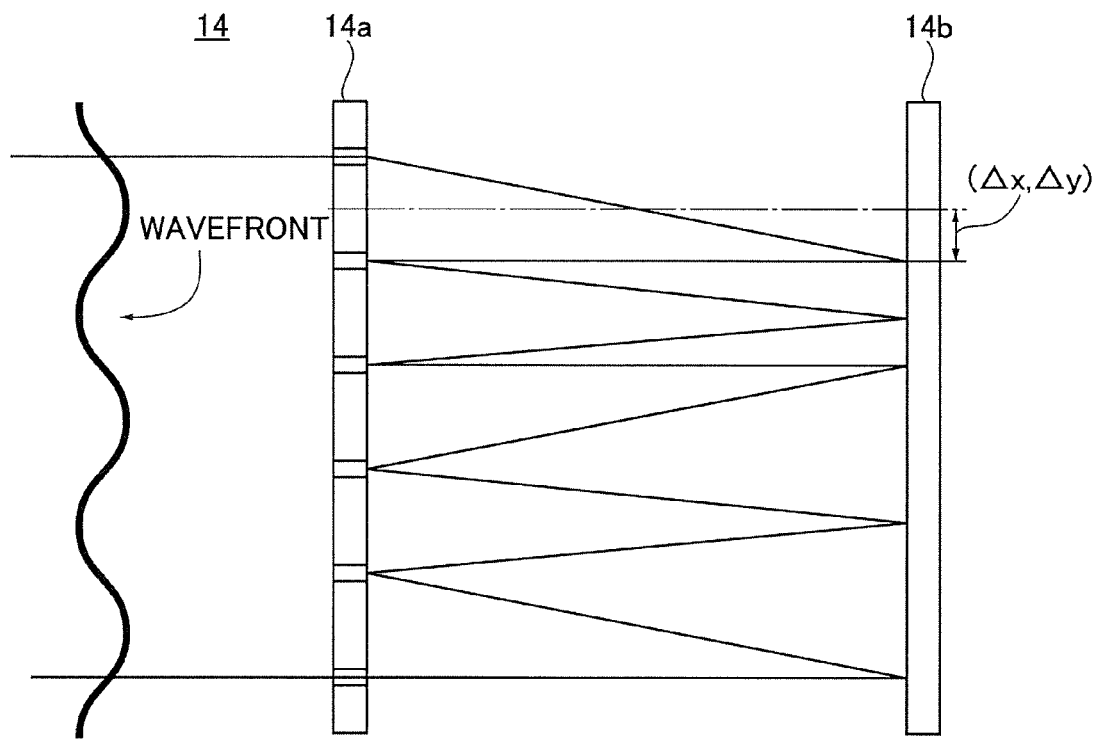
FIG. 5 is an explanatory view illustrating a wavefront sensor of a photographing control system according to the first embodiment.

FIG. 5 illustrates the wavefront sensor 14 of the photographing control system.

Referring to FIG. 5, the wavefront sensor 14 includes, for example, the Hartmann plate 14a in which micro-Fresnel lenses are aligned in a lattice-like configuration, and the two-dimensional CCD 14b disposed parallel to the Hartmann plate 14a and separated from the Hartmann plate 14a at a predetermined interval.

The measurement of the wavefront aberration by the wavefront sensor 14b is performed by projecting a point light source onto the retina Ef or an amphiblestode of the eye E, dividing the reflected light from the retina into plural light fluxes with the Hartmann plate 14a, and measuring point-image positions of the respective light fluxes by the two-dimensional CCD 14b. Then, by comparing the measured point-image positions with point-image positions according to a non-aberration eye, the wavefront aberration appears as an amount of displacement (Δx, Δy) of each point-image. The displacement amounts (Δx, Δy) of the respective point-images correspond to an inclination of a configuration of the wavefront aberration. Thus, the wavefront aberration is restored by the displacement amounts. Therefore, it is possible to measure the wavefront aberration with high accuracy, by setting of the number of the micro Fresnel lenses aligned in the lattice-like configuration and setting of the number of elements of the two-dimensional CCD 14b.

The wavefront sensor 14 measures an initial wavefront aberration before the compensation and the residual aberration in each repetition of the compensation. A result of the measurement of the initial wavefront aberration and the residual aberration in each repeated compensation by the wavefront sensor 14 is used as input information of a compensation algorithm for a higher order wavefront aberration, which deforms the deformable mirror 9 into a phase configuration opposite to that of the wavefront. Here, the result of the aberration measurement by the wavefront aberration is used also as input information for compensation of a lower order wavefront aberration, which compensates a spherical diopter power component and an astigmatism power component within the wavefront aberration generated due to flexing characteristics of the eye E.

Figure 6:
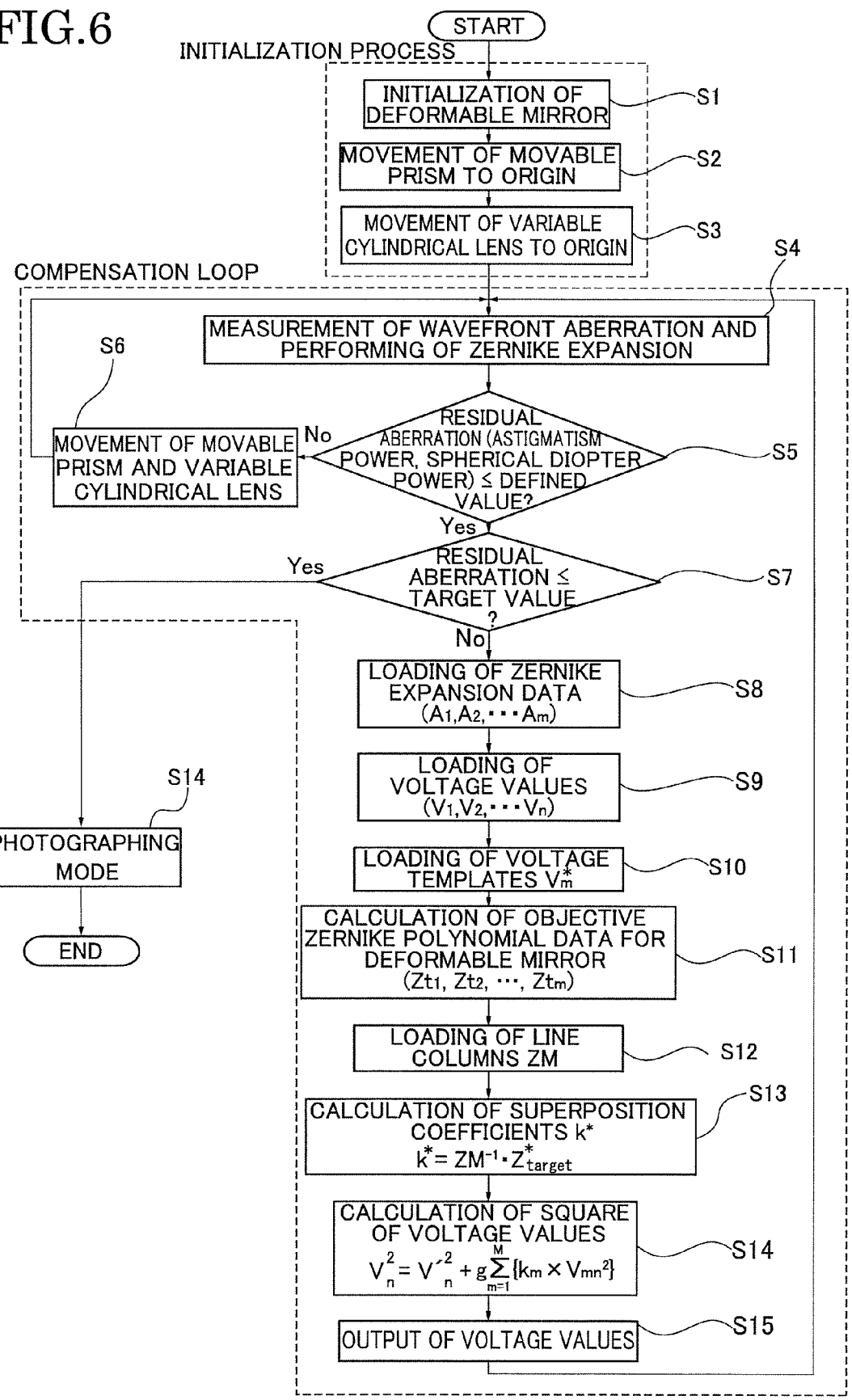
FIG. 6 is a flowchart illustrating a flow of a control processing for compensating a wavefront aberration executed by a controller of the wavefront control system according to the first embodiment.

FIG. 6 is a flowchart illustrating a flow of a control processing for compensating the wavefront aberration executed by the controller 15 of the wavefront control system according to the first embodiment. Hereinafter, each step of the control processing will be described. The control processing for the compensation of the wavefront aberration is activated by manipulation by an operator of initiating observation, photographing and so forth of an image of the retina at the high magnification, for example.

Referring to FIG. 6, in a step S1, an initial voltage V0 is applied to all of the electrodes 9e of the deformable mirror 9 to perform initialization of the deformable mirror 9. More specifically, the thin-film mirror 9b of the deformable mirror 9 becomes unstable when a voltage of each of the electrodes 9e exceeds a voltage $V_p$ in which the interval between the thin-film mirror 9b and the electrodes 9e becomes ⅔, and thereby the electrodes 9e and the thin-film mirror 9b contact with each other, which may be hereinafter referred to as a phenomenon of pull-in. Therefore, in the present embodiment, the initial voltage V0 is set at a value slightly lower than that of the voltage $V_p$, which causes the pull-in, in a case in which the voltage having the same voltage value is applied to all of the electrodes 9e. Accordingly, an average value of the voltage for the entire electrodes is fixed at the initial voltage V0 in the subsequent control of the deformable mirror, whereby the pull-in phenomenon is prevented from occurring, and a range of control of the voltage is widened, and at the same time, a fluctuation in the spherical diopter power component (n, m)=(2, 0) is suppressed.

In a step S2, after the initialization of the deformable mirror in the step S1, the movable prism 6 of the autofocusing system, which corrects the spherical diopter power component such as myopia, hyperopia and so forth within the wavefront aberration, is moved to an initial position or a point of origin.

In a step S3, after the movement of the movable prism 6 to the origin in the step S2, the variable cylindrical lens 3, which corrects the astigmatism power component within the wavefront aberration, is moved to an initial position or a point of origin. It is to be noted that the steps S1 to S3 correspond to an initialization process.

In a step S4, the wavefront aberration is measured on the basis of a signal supplied from the wavefront sensor 14 with respect to respective expansion modes according to Zernike polynomials, after the movement of the variable cylindrical lens 3 to the origin in the step S3, movement of the movable prism 6 and the variable cylindrical lens 3 in a step S6, or an output of voltage values in a step S15.

Hereinafter, the expansion modes according to the Zernike polynomials will be described.

A difference between the wavefront aberration of the eye E and a wavefront aberration to be compensated, i.e., the residual aberration, is expanded by the Zernike polynomials as follows.

$$W(r;\theta) = \Sigma \{A_m \times Z_m(r;\theta)\}$$

where W (r, θ) is the residual aberration, $Z_m$ (r, θ) is the Zernike polynomial of the expansion mode "m", and $A_m$ is an amplitude value of the expansion mode according to each of the Zernike polynomials. Here, with reference to FIG. 7, the expansion modes "m" are assigned with numbers, subsequently from lower order modes, from m=1 to m=M (M is a maximum value of higher order modes), with respect to respective orders "n" (0 to 10) and respective mode forms "m" (−10 to 0 to 10).

Figure 7:
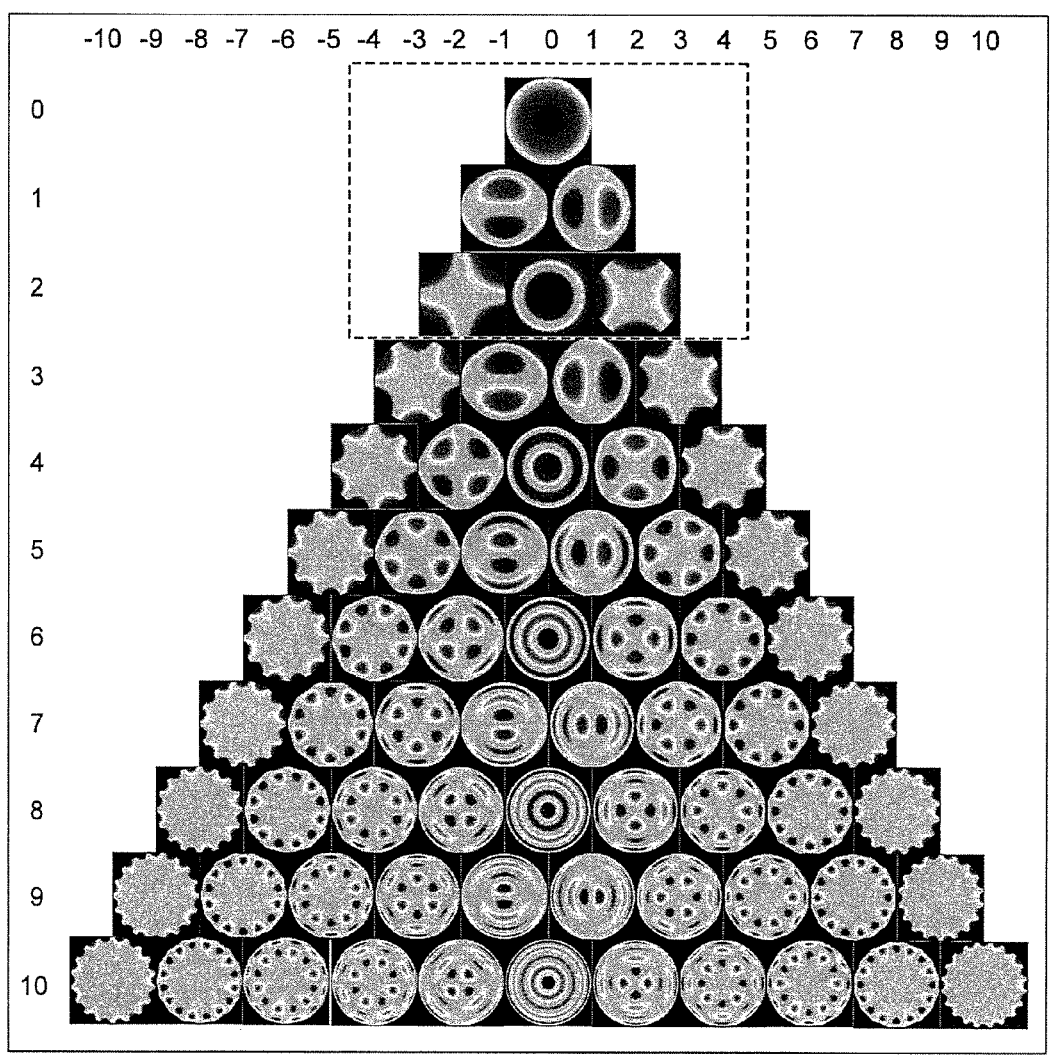
FIG. 7 is a diagram illustrating expansion modes according to zero-order to 10th order Zernike polynomials.

In addition, the "respective expansion modes according to the Zernike polynomials" in the present embodiment refers to modes expanded by each of the Zernike polynomials when a wavefront aberration is decomposed by Zernike polynomials often used in a field of optics. Each of the expansion modes corresponds to independent shape of wavefront, i.e., modes. FIG. 7 illustrates each of the expansion modes according to the zero-order to 10th order Zernike polynomials, and each expansion mode corresponds to a classical wavefront aberration. Therefore, it is possible to know components of the aberration.

In a step S5, after the wavefront measurement and the Zernike expansion in the step S4, whether or not the residual aberration (astigmatism power component, spherical diopter power component) is equal to or less than a defined value is judged.

In the present embodiment, the defined value is determined in consideration of the 2nd order in the expansion modes according to the Zernike polynomials. More specifically, the defined value is determined based on the six lower order modes within a frame illustrated in FIG. 7, for example. The 6 lower order modes can be represented by (n, m)=(0, 0), (1, −1), (1, 1), (2, −2), (2, 0) and (2, 2), in terms of a relationship between the orders "n" and the mode forms "m". It is to be noted that zero-order of n=0 is a phase and 1st order is a tilt, which are irrelevant to a blur of an image.

In the step S5, when the residual aberration is judged not equal to or less than the defined value (No in the step S5), the flow moves to the step S6, whereas when the residual aberration is judged equal to or less than the defined value (Yes in the step S5), the flow moves to a step S7.

In the step S6, after the judgment as "the residual aberration>the defined value" in the step S5, the spherical diopter power component ((n, m)=(2, 0)) within the wavefront aberration is adjusted by moving the movable prism 6 of the autofocusing system, and the astigmatism power component ((n, m)=(2, −2), (2, 2)) within the wavefront aberration is adjusted by moving the variable cylindrical lens 3.

This compensation of the lower order wavefront aberration adjusts the spherical diopter power component and the astigmatism power component within the wavefront aberration to be decreased. More specifically, the compensation of the lower order wavefront aberration is performed by moving the movable prism 6 and the variable cylindrical lens 3 as in a case in which correction is performed with spectacle lenses, contact lenses and so forth, in accordance with a degree of myopia, a degree of hyperopia, a degree of astigmatism detected by the wavefront sensor 14.

Here, a loop of the compensation of the lower order wavefront aberration in an order from the step S5, the step S6 and the step S4 is repeated until the residual aberration (astigmatism power component, spherical diopter power component) is judged to be equal to or less than the defined value in the step S5.

In a step S7, after the judgment as "the residual aberration (astigmatism power component, spherical diopter power component)≦the defined value" in the step S5, whether or not the residual aberration is equal to or less than a target value is judged.

In the present embodiment, the target value is determined on the basis of an allowable wavefront aberration in which a sharp image is obtainable when the retina Ef, as an object subjected to the aberration compensation, is observed, photographed and so on, by a set magnification. For example, the target value is determined in consideration of the orders in the expansion modes by the Zernike polynomials, at least to the 6th order. In addition, when there is a demand for high magnification, the target value is determined based on the orders from 6th to 10th in the expansion modes by the Zernike polynomials, in accordance with the magnification.

More specifically, when, for example, photographing a visual cell of the retina Ef having 2 μm to 5 μm, the wavefront aberration in the analysis area in a case of the optical system according to the present embodiment is less than 0.05 μm in an actual measurement value of a RMS (Root Mean Square), in order to observe such a visual cell. Thus, the target value is determined on the basis of that actual measurement value according to the RMS.

Here, the RMS is one of indexes of the wavefront aberration, and represents a standard deviation or the square root of a variance between an ideal wavefront aberration and an actual wavefront aberration.

In the step S7, when the residual aberration is judged not equal to or less than the target value (No in the step S7), the flow moves to the step S8, whereas when the residual aberration is judged equal to or less than the target value (Yes in the step S7), the flow moves to a step S16.

In a step S8, after the judgment as "the number of times of the compensation loop≦the set number of times n" in the step S7, the amplitude values ($A^*=A_1, A_2, \ldots, A_m$) in the respective expansion modes are loaded from expansion data of the Zernike polynomials of the residual aberration calculated in the step S4. Hereinafter, the asterisk "*" represents a vector.

In a step S9, after the loading of the amplitude values ($A^*=A_1, A_2, \ldots, A_m$) in the respective expansion modes in the step S8, the voltage values ($V^*=V_1, V_2, \ldots, V_n$) applied to the respective electrodes 9e at the loading of the amplitude values are loaded.

It is to be noted that the voltage values ($V^*=V_1, V_2, \ldots, V_n$) are used in the previous control of the electrodes 9e. The values of the initial voltage V0 described in the step S1 are used in the initial control.

In a step S10, after the loading of the voltage values ($V^*=V_1, V_2, \ldots, V_n$) in the step S9, voltage templates $Vm^*$ to be used in the current arithmetic processes are loaded from the previously-stored voltage templates $Vm^*$ (voltage template storing means), which are determined from a result of experiments. In the present embodiment, the voltage templates are stored in a memory included in the controller 15. Alternatively, the voltage templates may be stored in an external recording medium, which can be detachably connected or remotely connected to the controller 15.

Figure 8:
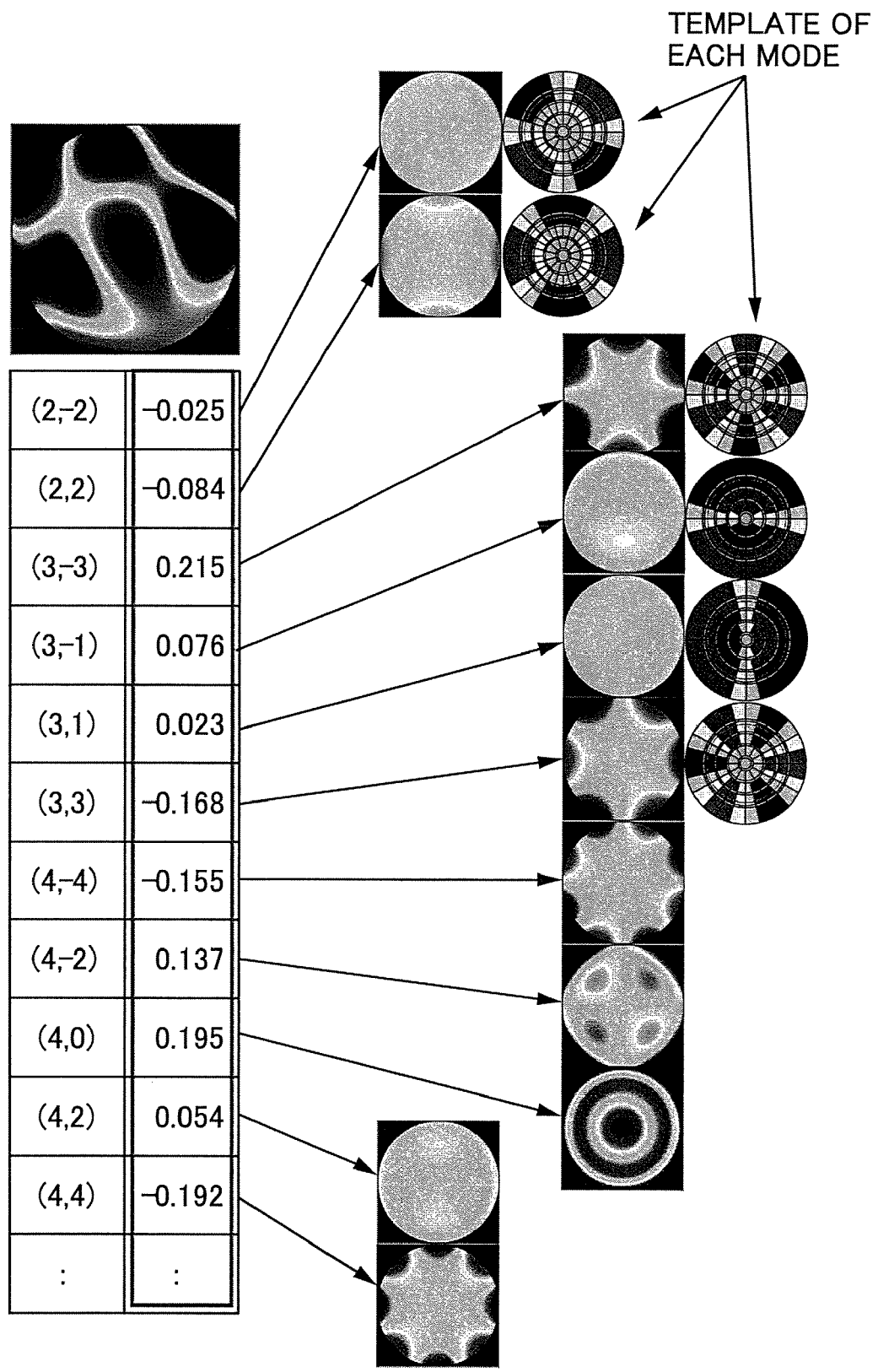
FIG. 8 illustrates one example of voltage templates in the respective expansion modes used in the wavefront aberration compensating apparatus according to the first embodiment.

Referring to FIG. 8, for example, the voltage template $Vm^*$ is data on alignment of voltage set for each of the expansion modes according to the Zernike polynomials of the wavefront aberration and which induces each of the corresponding expansion modes. In addition, the voltage template $Vm^*$ is provided for each of the expansion modes from the lower order modes to the higher order modes subjected to the compensation (preferably 6th order or higher), excluding the six lower modes (n, m)=(0, 0), (1, −1), (1, 1), (2, −2), (2, 0) and (2, 2) as the modes subjected to the compensation of the lower order wavefront aberration.

In a step S11, after the loading of the voltage templates Vm* in the step S10, objective Zernike polynomial data $Z^*_{target}$ as the objective configuration generated by the deformable mirror 9 are calculated by using $Z^*_{target}=(Zt_1, Zt_2, Zt_3, Zt_4, \ldots, Zt_m)$.

More specifically, the residual aberration of the light flux having passed through the deformable mirror 9 is represented as:

$$A^* + Z^*_{target}$$

Therefore, when the deformable mirror 9 is to be controlled such that the residual aberration of the light flux having passed through the deformable mirror 9 is eliminated, the following is established.

$$Z^*_{target} = -A^*$$

In a step S12, after the calculation of the objective Zernike polynomial data $Z^*_{target}$ in the deformable mirror 9 in the step S11, line-columns ZM previously calculated are loaded.

Here, the line-columns ZM are amplitude vector data of the actual wavefront aberration generated when the voltages of the voltage templates $V_m^*$ inducing the particular Zernike expansion mode "m" are applied to the electrodes 9e, which are arranged in a matrix form and determined by a result of experiments. Thereby, ideally, only a single Zernike expansion mode should be generated, although actually, other Zernike expansions mores are mixed, due to imperfection of the templates. Due to such imperfection of the templates, the line-columns ZM are set.

As described above, the line-columns ZM are defined by a following formula.

$$ZM = \begin{pmatrix} Z_{1,1} & Z_{2,1} & \cdots & Z_{m,1} \\ Z_{1,2} & Z_{2,2} & & Z_{m,2} \\ \vdots & & & \vdots \\ Z_{1,m} & Z_{2,m} & \cdots & Z_{m,m} \end{pmatrix}$$

Alternatively, in order to speed up the calculation by simplification, the line columns ZM may also be defined by a following formula (1).

$$ZM \approx \begin{pmatrix} Z_{1,1} & 0 & \cdots & 0 \\ 0 & Z_{2,2} & & 0 \\ \vdots & & & \vdots \\ 0 & 0 & \cdots & Z_{m,m} \end{pmatrix} \quad (1)$$

Alternatively, a flow of the calculation can also be proceeded by a following formula (2) in which the voltage templates are normalized, and in which $Z_{m,m}$ is set to be one.

$$ZM \approx \begin{pmatrix} 1 & 0 & \cdots & 0 \\ 0 & 1 & & 0 \\ \vdots & & \ddots & \vdots \\ 0 & 0 & \cdots & 1 \end{pmatrix} \quad (2)$$

In a step S13, after the loading of the line-columns ZM in the step S12, superposition coefficients k* are calculated from a following formula.

$$k^* = ZM^{-1} \cdot Z^*_{target}$$

This formula is for obtaining such superposition coefficients k* that the following is established.

$$Z^*_{target} \approx ZM \cdot k^*$$

Here, in a case of the formula (1) which ignores the imperfection of the templates, the following is established.

$$k^* = \left( \frac{Z_{t1}}{Z_{1,1}} \quad \frac{Z_{t2}}{Z_{2,2}} \quad \cdots \quad \frac{Z_{tm}}{Z_{m,m}} \right)$$

Therefore, when the deformable mirror 9 is so set that the aberration is eliminated with the deformable mirror 9 in the case of the formula (2), the following is represented.

$$k^* = -A^*$$

In a step S14, after the calculation of the superposition coefficients k* in the step S13, the square values $V_n^2$ of the voltage values $V_n$ for obtaining a configuration of the thin-film mirror 9b of the deformable mirror 9, that eliminates the aberration, are calculated from a following formula, determined since the square of the voltage is virtually in proportional to the displacement amount.

$$V_n^2 = V_n'^2 + g\Sigma\{k_m \times V_{mn}^2\}$$

where the $V_n$ loaded in the step S9 is replaced by $V_n'$ in the previous control cycle, and "g" is a feedback gain or a compensation coefficient determined from experiments, which is changeable for each orbicular zone or each electrode. The feedback gain "g" is designed at a value such that no divergence is occurred in the correction of the higher order wavefront aberration, and that the residual aberration becomes equal to or less than the target value with good responsiveness and reduced number of repeated times of the compensation loop.

In the step S15, after the calculation of the square of the voltage values in the step S14, the voltage values $V_n$ are determined by the square voltage values $V_n^2$ obtained in the step S14, and driving instructions for applying the determined voltage values $V_n$ to the respective electrodes 9e are outputted to the driver 16. The flow returns to the step S4 after the completion of the step S15, to structure a compensation loop of the higher order wavefront aberration.

In a step S16, after the judgment as "the residual aberration≦the target value" in the step S7, a photographing mode for carrying out the high magnification photographing of the retina Ef is performed.

In the flowchart illustrated in FIG. 6, the steps S1 to S6 correspond to lower order wavefront aberration compensating means, the steps S8 to S14 correspond to voltage calculating means, and the steps S4, S5, and S7 to S15 correspond to deformable mirror controlling means.

Now, operation according to the present embodiment will be described.

Hereinafter, operation performed by the wavefront aberration compensating apparatus according to the present embodiment will be described by sections referred to as "Operation on Compensation Control of Lower Order Wavefront Aberration", "Operation on Compensation Control of Higher Order Wavefront Aberration", and "Operation on Compensation of Wavefront Aberration by the use of Deformable Mirror and Compensation Algorithm according to the First Embodiment".

[Operation on Compensation Control of Lower Order Wavefront Aberration]

Referring to the flowchart of FIG. 6, the flow moves in an order of the steps S1, S2, and S3, when the control for the compensation of the wavefront aberration is initiated. More specifically, the initialization process in which the initialization of the deformable mirror 9 is performed in the step S1, the movement of the movable prism 6 to the origin or to a default position is performed in the step S2, and the movement of the variable cylindrical lens 3 to the origin or to a default position is performed in the step S3, are carried out.

In the step S1, a reason why the initial voltage V0 is applied to all of the electrodes 9e to perform the initialization of the deformable mirror 9 with a state of displacement of the deformable mirror 9 closer to an amount of initial displacement of the deformable mirror 9, is to increase responsiveness for the convergence toward the objective wavefront aberration while suppressing hunting in control, by employing a mode of deformation of the deformable mirror 9 in which only a direction in which the pulling force of the thin-film mirror 9b by the electrodes 9e is decreased, in the later-described compensation of the wavefront aberration utilizing the deformable mirror 9.

After the step S3, the flow moves in an order of the steps S4 and S5. The flow in an order of the steps S5, S6, and S4 is repeated until the judgment as "the residual aberration≦the defined value" is established in the step S5.

More specifically, when the judgment "the residual aberration>the defined value" is established in the step S5, the flow of adjusting the spherical diopter component in the wavefront aberration by moving the movable prism 6 of the autofocusing system and of adjusting the astigmatism power component in the wavefront aberration by moving the variable cylindrical lens 3 in the step S6, and of measuring the wavefront aberration after the adjustment in the step S4, is repeated.

When the judgment as "the residual aberration≦the defined value" is established in the step S5, the loop of compensation of the lower order wavefront aberration, in which the flow of proceeding in the order of the steps S5, S6, and S4 is repeated, is finished, and the flow moves on to the process of compensating the higher order wavefront aberration in and after of the step S7.

Accordingly, in the embodiment of the invention, the compensation loop for the lower order wavefront aberration including the steps S4, S5, and S6, which compensates the spherical diopter component and the astigmatism power component in the wavefront aberration generated due to the flexing characteristics of the eye E, is provided. Thus, in the later-described compensation loop for the higher order wavefront aberration, a wavefront aberration component remained after the compensation of the lower order wavefront aberration by the compensation loop for the lower order wavefront aberration, and a wavefront aberration component higher in order than the orders subjected to the lower order wavefront aberration compensation, are compensated by deforming the deformable mirror 9.

Therefore, a burden in the compensation of the wavefront aberration in the compensation loop for the higher order wavefront aberration is reduced significantly. Hence, it is possible to increase the responsiveness for the convergence of the residual aberration to be equal to or less than the target value, and to reduce the number of times of the repetition of the compensation in the compensation loop for the higher order wavefront aberration.

[Operation on Compensation Control of Higher Order Wavefront Aberration]

Referring to FIG. 6, when the judgment as "the residual aberration (astigmatism power, spherical diopter power)≦the defined value" is established in the step S5, the flow proceeds in an order of the steps from the step S5 to S7, S8, S9, S10, S11, S12, S13, S14, and S15.

More specifically, in the step S8, the amplitude values ($A^*=A_1, A_2, \ldots, A_m$) in the respective modes are loaded from the expansion data of the Zernike polynomials of the residual aberration. Then, in the step S9, the voltage values ($V^*=V_1, V_2, \ldots, V_n$) applied to the respective electrodes 9e at the time of the loading of the amplitude values are loaded. In the step S10, the voltage templates $V_m^*$ corresponding to the Zernike polynomial mode "m" to be compensated in the current occasion are loaded. Thereafter, in the step S11, the objective Zernike polynomial data $Z^*_{target}$ are calculated from the formula: $Z^*_{target}=(Zt_1, Zt_2, Zt_3, Zt_4, \ldots, Zt_m)$. In the step S12, the previously-calculated line-columns ZM are loaded, and in the step S13, the superposition coefficients k* are calculated. In the step S14, the square values $V_n^2$ of the voltage values $V_n$ for obtaining the objective mirror deformation are calculated. In the step S15, the voltage values $V_n$ are determined by the square voltage values $V^2$, and driving instructions for applying the determined voltage values $V_n$ to the respective electrodes 9e are outputted to the driver 16.

The flow returns to the step S4 after the output of the voltage values in the step S15. In the step S4, the wavefront aberration after the output of the voltage values $V_n$, determined in the current arithmetic processes, to the respective electrodes 9e is measured. Then, the flow proceeds in the order of steps S5 and S7. Thereafter, the flow which proceeds in an order of the steps S8, S9, S10, S11, S12, S13, S14, S15, S4, S5, and S7 in the flowchart of FIG. 6 is repeated as long as the judgment as "the residual aberration>the target value" is established in the step S7. In other words, a compensation loop of the higher order wavefront aberration is structured during when the judgment as "the residual aberration>the target value" is established.

When the judgment as "the residual aberration≦the target value" is established in the step S7, the flow proceeds from the step S7 to the step S16. In the step S16, the flow moves on to the photographing mode in which the high magnification photographing of the retina Ef is carried out.

Therefore, according to the wavefront aberration compensating apparatus of the first embodiment, the superposition coefficients k* of the respective expansion modes are calculated, and the voltage values $V_n$ to be applied to the electrodes 9e are calculated from the stored voltage templates $V_m^*$ such that the wavefront aberration obtained by the wavefront sensor 14 becomes a desired aberration, in the steps S8 to S14. In the compensation loop of the higher order wavefront aberration, the control in which the compensation for the configuration of the thin-film mirror of the deformable mirror 9 is repeated is performed on the basis of the calculated voltage values $V_n$, such that the wavefront aberration of the light flux measured by the wavefront sensor is suppressed.

[Operation on Compensation of Wavefront Aberration By the Use of Deformable Mirror and Compensation Algorithm According to the First Embodiment]

First, a structure of the deformable mirror 9 and a calculation method for the control voltages of the deformable mirror 9 will be described.

The electrodes 9e are arranged to face the grounded conductive thin-film mirror 9b in the deformable mirror 9. The thin-film mirror 9b of the deformable mirror 9 is distorted due to an electrostatic force by application of the voltage to each of the electrodes 9e. When the voltages are applied to the respective electrodes located under a part of the thin-film mirror 9b where a dent or deformation is to be formed, the thin-film mirror 9b is dented or deformed. Here, an amount of the dent or the deformation is substantially in proportional to square of the voltage.

A configuration or a shape generated by the deformable mirror 9 is determined by an alignment pattern of the electrodes 9e, the number of the electrodes 9e, and a level of the voltage applied to each of the electrodes 9e. More specifically, a large variety of configurations or shapes of the deformable mirror 9 can be provided when the number of the electrodes 9e is increased, although this takes extremely long time to calculate the voltages. Thus, the diversity of the configurations for the compensation and a speed of processing have a tradeoff relationship, when the realtime compensation is to be performed.

In addition, the calculation of the control voltages for generating such a configuration of the deformable mirror 9 which compensates the measured wavefront aberration is extremely difficult. In particular, the thin-film mirror 9b is a continuum. Thus, when the voltage is applied to one electrode, not only a part of the thin-film mirror in the vicinity of the voltage deforms but the entire surface of the mirror is influenced thereby. Therefore, in a conventional technology, a method in which a configuration of an entire surface of a mirror at the time when one voltage is applied is previously recorded, and in which the voltage for each of the electrodes is so determined that superposition of the configurations of the entire surfaces becomes nearest to an objective configuration, is employed.

According to the wavefront aberration compensating apparatus of the first embodiment, the deformable mirror 9 has the extremely large number of electrodes 9e, i.e., a total of 85 electrodes 9e, as illustrated in FIG. 4. Therefore, since the time required by the conventional calculation method of the driving voltages is long, a simplified method, i.e., the compensation algorithm, which calculates the driving voltages at high speed is expanded according to the present embodiment.

First, a conventional compensation algorithm in which a voltage template is provided for each electrode will be described.

A following formula is previously provided as a voltage alignment (hereinafter also referred to as a voltage template) which applies a voltage only to one electrode "n".

$$V_1^* = (V\ 0\ 0\ \cdots\ 0\ 0)$$
$$\vdots$$
$$V_i^* = (0\ \cdots\ V\ \cdots\ 0\ 0)$$
$$\vdots$$
$$V_n^* = (0\ 0\ 0\ \cdots\ 0\ V)$$

In addition thereto, a data array $Z_n^*$ of a wavefront configuration in a case when the voltage template $V_n^*$ is applied is previously recorded per number of electrodes. Normally, amplitude data of each expansion mode "m" is utilized as data of the data array $Z_n^*$, by expanding wavefront data with Zernike polynomials. Accordingly, description will be made on the basis of the amplitude data $Z_{n,m}$ expanded by the Zernike polynomials. Note that the $Z_{n,m}$ can be based on other polynomial expansion, actual data on displacement of measuring point, and so on.

When the wavefront data $Z_n^*$ for each of the voltage templates $V_n^*$ in the case in which only one electrode is driven is referred to as influence vectors, the influence vectors $Z_n^*$ are represented as follows.

$$Z_1^* = (Z_{1,1}\ Z_{1,2}\ Z_{1,3}\ Z_{1,4}\ \cdots\ Z_{1,m})$$
$$\vdots$$
$$Z_i^* = (Z_{i,1}\ Z_{i,2}\ Z_{i,3}\ Z_{i,4}\ \cdots\ Z_{i,m})$$
$$\vdots$$
$$Z_n^* = (Z_{n,1}\ Z_{n,2}\ Z_{n,3}\ Z_{n,4}\ \cdots\ Z_{n,m})$$

Additionally, when such influence vectors $Z_n^*$ arranged per number of the voltage templates are referred to as influence line-columns ZM, the influence line-column ZM are represented as follows.

$$ZM = \begin{pmatrix} Z_{1,1} & Z_{2,1} & \cdots & Z_{n,1} \\ Z_{1,2} & Z_{2,2} & & Z_{n,2} \\ \vdots & & & \vdots \\ Z_{1,m} & Z_{2,m} & \cdots & Z_{n,m} \end{pmatrix}$$

Moreover, when the objective configuration generated by the deformable mirror is represented by:

$Z^*_{target} = (Zt_1, Zt_2, Zt_3, Zt_4, \ldots, Zt_m)$, such a value in which a linear combination of an influence function becomes nearer to the objective configuration is to be obtained.

When superposition coefficients at the time of the linear combination are represented by:

$k^* = (k_1, k_2, \ldots, k_n)$, a following formula is established.

$$Z^*_{target} \approx ZM \cdot k^*$$

$$\begin{pmatrix} z_{t1} \\ z_{t2} \\ \vdots \\ z_{tm} \end{pmatrix} \approx \begin{pmatrix} Z_{1,1} & Z_{2,1} & \cdots & Z_{n,1} \\ Z_{1,2} & Z_{2,2} & & Z_{n,2} \\ \vdots & & & \vdots \\ Z_{1,m} & Z_{2,m} & \cdots & Z_{n,m} \end{pmatrix} \cdot \begin{pmatrix} k_1 \\ k_2 \\ \vdots \\ k_n \end{pmatrix}$$

Such superposition coefficients "$k^*$" in which an error between a result of calculation in a right side and a result of calculation on a left side becomes the least in the above formula are to be obtained. By using the value of the obtained superposition coefficients "$k^*$" to actually superpose the voltage templates, so as to obtain compensation voltages $V^*$. The superposition of the voltage templates is carried out in consideration of a displacement which is in proportional to square of a voltage.

$$\begin{pmatrix} V_1^2 \\ V_2^2 \\ \vdots \\ V_n^2 \end{pmatrix} = \begin{pmatrix} V^2 & 0 & \cdots & 0 \\ 0 & V^2 & & 0 \\ \vdots & & & \vdots \\ 0 & 0 & \cdots & V^2 \end{pmatrix} \cdot \begin{pmatrix} k_1 \\ k_2 \\ \vdots \\ k_n \end{pmatrix}$$

The foregoing is the calculation of the voltage for the aberration compensation by the conventional compensation algorithm in which the voltage template is provided for each of the electrodes.

What takes time in the conventional calculation is the working-out of the superposition coefficients k*, and a problem is that it takes extremely long time when the number of the electrodes "n" is increased. Thus, it is crucial if the number of the electrodes is large in a case in which realtime control is to be carried out.

Now, a method of voltage calculation according to the present embodiment will be described.

In the present embodiment, the voltage template $V_m^*$ which induces the particular Zernike expansion mode "m" is used. When the number of the Zernike expansion modes subjected to the compensation is "M", m-pieces of voltage templates $V_m^*$ are to be generated.

$$V_1^* = (V_{1,1} \quad V_{1,2} \quad \cdots \quad V_{1,n})$$
$$V_m^* = (V_{m,1} \quad V_{m,2} \quad \cdots \quad V_{m,n})$$

Here, wavefront configuration data $Z_m^*$ (equivalent to the above-described influence vector) corresponding to each of the voltage templates $V_m^*$ and the line-columns ZM, in which the wavefront configuration data $Z_m^*$ are aligned, are defined as follows.

$$Z_1^* = (Z_{1,1} \quad Z_{1,2} \quad \cdots \quad Z_{1,m})$$
$$\vdots$$
$$Z_m^* = (Z_{m,1} \quad Z_{m,2} \quad \cdots \quad Z_{m,m})$$

$$ZM = \begin{pmatrix} Z_{1,1} & Z_{2,1} & \cdots & Z_{m,1} \\ Z_{1,2} & Z_{2,2} & & Z_{m,2} \\ \vdots & & & \vdots \\ Z_{1,m} & Z_{2,m} & \cdots & Z_{m,m} \end{pmatrix}$$

In addition, the superposition coefficients k* are determined by the number of the voltage templates $V_m^*$. Thus, in the present embodiment of the invention, the number of elements is not the n-pieces (the number of electrodes) but the m-pieces (the number of expansion modes subjected to compensation).

Therefore, an amount of calculation in a case of obtaining the superposition coefficients k* by a formula:

$Z^*_{target} \approx ZM \cdot k^*$ is determined not by the number of electrodes "n" but the number of the expansion modes "m" subjected to the compensation. Hence, it is possible to reduce the calculation time significantly when a device having the large number of electrodes is used for the deformable mirror 9.

Additionally, components other than a major component of the wavefront configuration data for each of the expansion modes can be ignored. A following formula is represented when those components are approximately ignored.

$$Z_1^* \approx (Z_{1,1} \quad 0 \quad \cdots \quad 0)$$
$$Z_2^* \approx (0 \quad Z_{2,2} \quad \cdots \quad 0)$$
$$\vdots$$
$$Z_m^* \approx (0 \quad 0 \quad \cdots \quad Z_{m,m})$$

Thus, the influence line-columns ZM are represented by a following formula.

$$ZM \approx \begin{pmatrix} Z_{1,1} & 0 & \cdots & 0 \\ 0 & Z_{2,2} & & 0 \\ \vdots & & & \vdots \\ 0 & 0 & \cdots & Z_{m,m} \end{pmatrix}$$

An accuracy in the compensation voltages is decreased when the above formula is used, but the superposition coefficients k* are obtainable easily. Therefore, it is possible to achieve speed-up of the realtime compensation in which the device having the large number of electrodes is used.

A concrete example will now be described.

(1) Observation of Retina at High Magnification

As one example, in a case of observing the retina Ef at high magnification, whether or not the observation can be accomplished is determined by sharpness or a degree of blur of a photographed image. The sharpness or the blur is determined by a diffraction limit, which depends on an optical system, and by the wavefront aberration. For example, when photographing the visual cell of the retina having 2 μm to 5 μm, the wavefront aberration in the analysis area in a case of the optical system according to the present embodiment is less than 0.05 μm in the actual measurement value of the RMS (Root Mean Square), in order to observe such a visual cell.

(2) The Number of Times of Repeated Compensation

Figure 9:
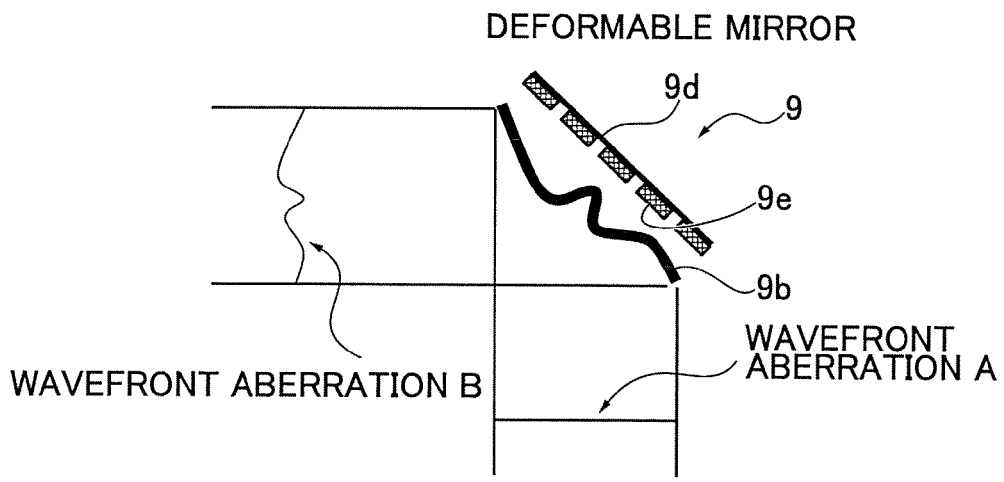
FIG. 9 is an explanatory view illustrating an operation of the compensation of the wavefront aberration in the deformable mirror.

When the retina Ef of the eye E is to be photographed, a duration time in which a person can keep its eye open with good condition is several seconds for a person of shorter duration time, although such a duration time varies depending upon individuals. Thus, in order to complete a procedure from the adjustment to the photographing within seconds, it is important to reach the wavefront aberration A according to the aimed wavefront aberration illustrated in FIG. 9 from a state of the wavefront aberration B illustrated in FIG. 9 with the minimum possible number of times of the compensation.

In a case in which the compensation algorithm (the template method for each expansion mode) of the voltage patterns according to the first embodiment was employed, the number of times in which a residual aberration saturates, i.e., the number of times in which the residual aberration no longer moves, was 15 times to 50 times, and a reached value of the residual aberration, i.e., a value in which the residual aberration no longer moved, was considerably small. Therefore, it has found that an aimed wavefront aberration is reached at the reduced number of times of the repetition of the compensation.

Figure 10:
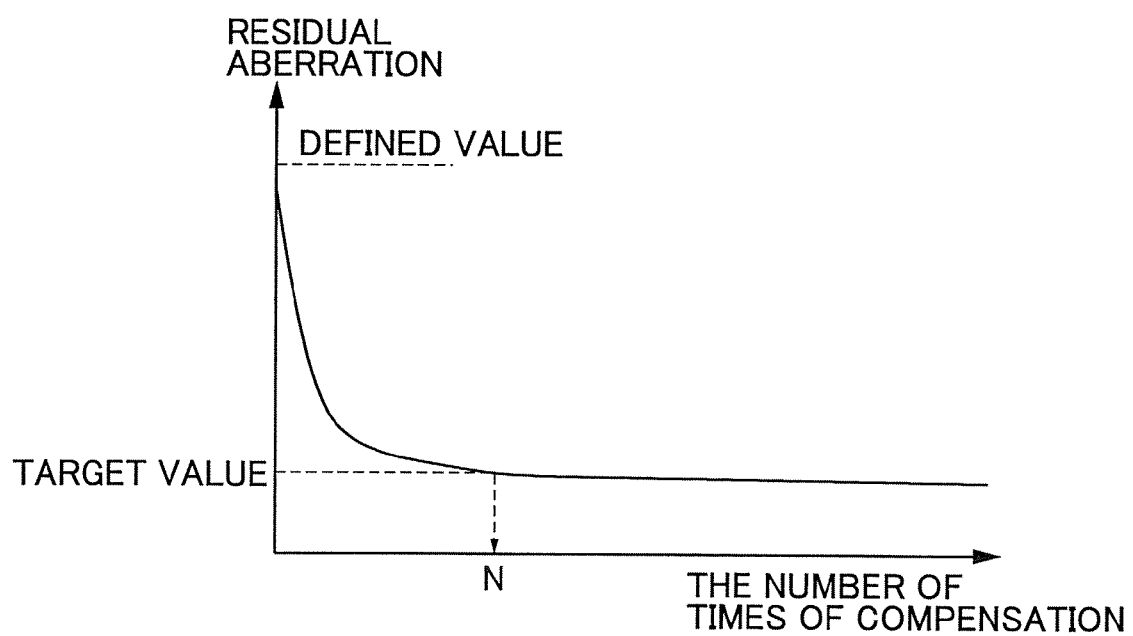
FIG. 10 is a diagram illustrating a relation of characteristics between the number of times of repetition of the compensation and a residual aberration in the compensation of the wavefront aberration in which the deformable mirror is used according to a compensation algorithm of the first embodiment.

In an experiment in which the target value of the residual aberration was set at 0.05 μm in the actual measurement value of the RMS, a residual aberration reached a target value by the number of times N of the compensation repeated for 5 times to 10 times, as illustrated in FIG. 10. Thereby, the residual aberration of equal to or less than 0.05 μm at the RMS, as a condition by which the sharp image is obtainable at 22-fold magnification (the magnification set due to an optical system of an experimental unit), was achieved.

In addition, the residual aberration became equal to or less than the target value by the repetition of the compensation repeated about 15 times, in an experiment in which the target value of the residual aberration was set less than 0.05 μm in the actual measurement value of the RMS. Therefore, the experiments have proved that the wavefront aberration compensating apparatus according to the present embodiment is an aberration compensation system which satisfies the above (1) and (2).

Second Embodiment

A second embodiment of the invention simplifies a method of calculating the superposition amplitude of each of the expansion modes, so as to speed up the arithmetic processes. Since a system structure of the second embodiment is the same or similar to that of the first embodiment, illustration and description thereon will not be provided in detail.

Figure 11:
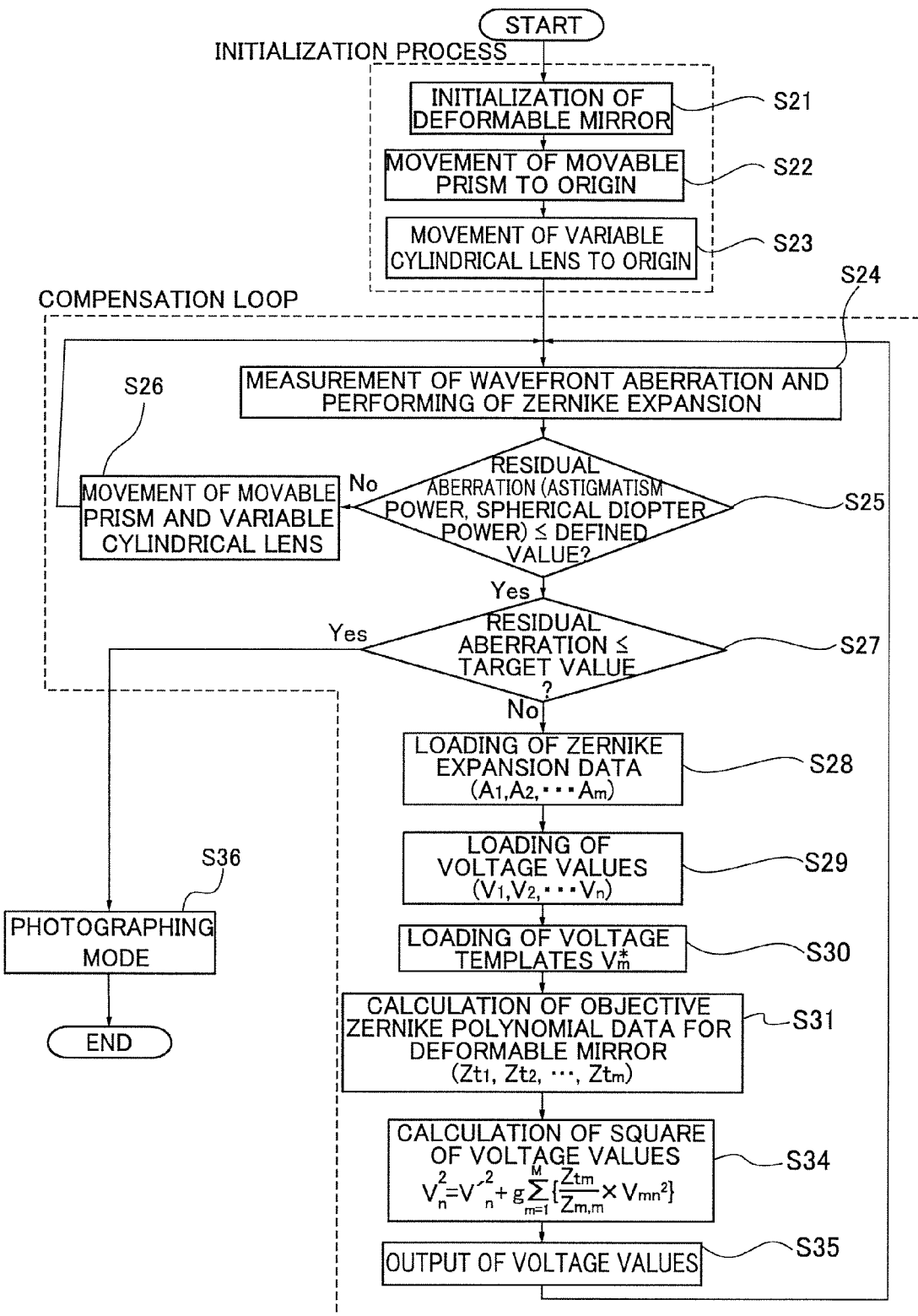
FIG. 11 is a flowchart illustrating a flow of a control processing for compensating the wavefront aberration executed by the controller of the wavefront control system according to a second embodiment.

FIG. 1 is a flowchart illustrating a flow of a control processing for compensating the wavefront aberration executed by the controller 15 of the wavefront control system according to the second embodiment. Hereinafter, each step of the flow will be described. The flowchart illustrated in FIG. 11 omits the steps S11 to S13 of the flowchart illustrated in FIG. 6 according to the first embodiment. In addition, since steps S21 to S31, S35, and S36 of the flowchart illustrated in FIG. 11 perform the same processes as in the steps S1 to S11, S15, and S16 of the flowchart of the FIG. 6, respectively, explanation thereof will not be given in detail.

In a step S34, after the loading of the voltage templates $V_m{}^*$ in the step S30, the square values $V_n{}^2$ of the voltage values $V_n$ for obtaining the configuration of the thin-film mirror 9b of the deformable mirror 9, that eliminates the aberration, is calculated from a following formula (3), determined since the square of the voltage is virtually in proportional to the displacement amount.

$$V_n{}^2 = V_n{}'^2 + g\Sigma\{(Zt_m/Z_{m,n}) \times V_{mn}{}^2\} \quad (3)$$

Alternatively, the above formula (3) may be used to calculate the square values $V_n{}^2$ of the voltage values $V_n$, when the simplified formula (1) in which only $Z_{mm}$ are remained and others are set at 0 (zero), is used with respect to the exact definition of the line-columns ZM, according to the description on the step S12 in FIG. 6 according to the first embodiment.

In addition, a following formula (4) may be used to calculate the square values $V_n{}^2$ of the voltage values $V_n$, when the simplified formula (2) in which the voltage templates are normalized to establish $Z_{mm}=1$, is used with respect to the formula (1) having simplified the line columns ZM, according to the description on the step S12 in FIG. 6.

$$V_n{}^2 = V_n{}'^2 + g\Sigma\{-A_m \times V_{mn}{}^2\} \quad (4)$$

Therefore, according to the exemplary embodiment of the invention described above, the superposition amplitude value of each of the expansion modes are determined, and the voltage value applied to each of the electrodes is calculated by using the stored voltage templates, such that the wavefront aberration obtained by the wavefront sensor becomes the desired aberration. In addition, the control in which the compensation for the configuration of the thin-film mirror of the deformable mirror is repeated is performed on the basis of the calculated voltage values, such that the wavefront aberration of the light flux measured by the wavefront sensor is suppressed.

More specifically, the wavefront measurement data in the analysis area of the thin-film mirror obtained by the wavefront sensor are represented as amplitude in the respective expansion modes expanded by polynomials of the wavefront aberrations. On the other hand, the voltage templates or voltage alignment data for obtaining configurations of the respective expansion modes are provided, which are then superposed to calculate the voltage alignment data which corresponds to the objective configuration. At this time, the superposition amplitude can be calculated as being equal to the amplitude in each of the expansion modes.

Thus, the template method for each expansion mode is employed, in which the voltage templates, which induce the corresponding expansion modes, are provided for the respective expansion modes of the polynomials of the wavefront aberrations, and in which the superposition amplitude are calculated as being equal to the amplitude of the expansion modes. Therefore, as compared with the conventional template method in which the configuration of the entire surface of the mirror at the time when one voltage is applied is previously recorded and in which the voltage for each of the electrodes is so determined that superposition of the configurations of the entire surfaces becomes nearest to the objective configuration, the amount of calculation becomes extremely small only if the amplitude in each of the expansion modes is obtained. Hence, the time required for one compensation processing is reduced.

In addition, the number of voltage templates depends on the number of expansion modes, without depending on the number of electrodes. Thus, the amount of calculation is significantly reduced even when the deformable mirror in which the number of electrodes for applying the voltages is large is used. In other words, the amount of calculation does not so increase even when the number of electrodes for applying the voltages is increased.

Moreover, by using the voltage templates inducing the respective expansion modes, it is possible to perform the compensation control of the wavefront aberration having high initial response in which the wavefront aberration becomes nearer to the target value rapidly in the initial stage of the compensation for the lower order wavefront aberration.

As described in the foregoing, the embodiment of the invention employs the compensation algorithm of the voltage patterns according to "the template method for each expansion mode", by which the deformable mirror is possible to reach the objective configuration in a short time. Hence, it is possible to suppress the residual aberration to be small with good responsiveness at the short time, and to obtain the extremely sharp image even if the high-magnification is set, even when the deformable mirror having the large number of electrodes to which the corresponding voltage is applied to each of those, is used for the compensation of the wavefront aberration.

In each of the above-described exemplary embodiments of the invention, the deformable mirror 9 includes a total of 85 electrodes 9e, although it is not limited thereto. The deformable mirror 9 may have more than 85 electrodes 9e, or may have less than 85 electrodes 9e. In other words, the number of the electrodes of the deformable mirror is not limited by the embodiments, which can be appropriately changed according to magnification required, a magnitude of the target value of the residual aberration, and so on. In addition, although it is preferable that the alignment pattern of the electrodes be so arranged that the wavefront aberrations corresponding to the expansion modes according to the Zernike polynomials are obtained easily, the alignment pattern of the electrodes also largely depends on the maximum order of the compensation orders of the wavefront aberrations. Therefore, the alignment pattern of the electrodes is not limited to the patterns described in the embodiments.

In each of the embodiments, the movable prism 6 as a prism is used for the focusing mechanism, although it is not limited thereto. It is to be noted that the focusing mechanism may be a mirror, or other suitable optical element. Alternatively, the focusing mechanism can be an optical element or an optical member having vertically-arranged planar mirrors, mutually.

In each of the embodiments, the compensation for the lower order wavefront aberration, which compensates the spherical diopter power component and the astigmatism power component generated due to the flexing characteristics of the eye E, is performed, since the object subjected to the compensation according to the embodiments is the eye E, although it is not limited thereto. In a case in which an object subjected to the compensation is other than the eye E, for example, when an object is a lens having a high order wavefront aberration provided in an optical path, the wavefront aberration compensation utilizing the deformable mirror may be immediately carried out without performing the compensation of the lower order wavefront aberration.

In each of the embodiments, the target value is determined based on the allowable wavefront aberration such that the sharp image of the retina Ef is obtained, since each of the embodiments is on the basis of wavefront aberration compensating apparatus provided in an optical system of the ophthalmologic unit which performs the observation and the photographing of the retina. However, the target value may be determined such that a particular aberration is obtained. Thereby, it is also possible to cause a model eye to have the particular aberration.

According to each of the above-described embodiments, the wavefront aberration compensating apparatus is applied to the ophthalmologic unit which performs the observation and the photographing of the retina, although it is not limited thereto. It is possible to apply the wavefront aberration compensating apparatus to various devices having an object, which requires the compensation of the wavefront aberration, in its optical system, other than the ophthalmologic unit. Such devices may be, for example but not limited to, a display, in particular a head-up display, a telescope, in particular an astrometric telescope, a laser irradiating unit, a microscope, an exposure unit, an optical disc (disk) unit, in particular an optical pickup device, a microfabrication unit, and other suitable devices in which a lens is used.

Accordingly, it is possible to achieve the following (1) to (14) from the above-described exemplary embodiments of the present invention.

(1) A wavefront aberration compensating apparatus, comprising: a deformable mirror which compensates a wavefront aberration of a light flux entered, the deformable mirror including a plurality of electrodes, and a thin-film mirror which changes a configuration thereof in accordance with a voltage value applied to each of the electrodes; an optical system provided with the deformable mirror, and including an object subjected to aberration compensation; a wavefront sensor which receives the light flux traveled through the object and the deformable mirror, and which measures the wavefront aberration of the light flux; a memory which stores therein a voltage template provided for each expansion mode according to a polynomial of wavefront aberration, as a voltage alignment data for the electrodes which induces the corresponding expansion mode of the expansion modes; and a controller configured to determine a superposition amplitude value of each of the expansion modes and calculate the voltage value applied to each of the electrodes by using the voltage templates stored in the memory, such that the wavefront aberration obtained by the wavefront sensor becomes a desired aberration, and to repeat compensation of the configuration of the thin-film mirror of the deformable mirror on the basis of the calculated voltage value, such that the wavefront aberration of the light flux measured by the wavefront sensor is suppressed.

Therefore, it is possible to suppress the residual aberration to be small with good responsiveness at the short time, and to obtain the extremely sharp image even if the high-magnification is set, even when the deformable mirror having the large number of electrodes to which the corresponding voltage is applied to each of those, is used for the compensation of the wavefront aberration.

(2) A wavefront aberration compensating apparatus according to (1), wherein the controller is configured to: apply an initial voltage to each of the electrodes such that an displacement amount of the thin-film mirror becomes an initial displacement amount; and control the configuration of the thin-film mirror created according to a voltage pattern generated for the electrodes to be a configuration which negates a configuration of the wavefront aberration of the light flux entered through the object, such that the wavefront aberration included in the light flux after reflection from the deformable mirror is suppressed to be small.

Therefore, it is possible to perform the control for the compensation of the wavefront aberration in which the hunting in the control is suppressed and having the high responsiveness and convergence, in the compensation control of the wavefront aberration utilizing the deformable mirror, by performing the initialization process of the deformable mirror by which the initial displacement amount is given previously and by fixing the average voltage of the electrodes to the initial voltage. In addition, it is possible to increase a dynamic range of the compensation by increasing the initial displacement amount to the extent in which the pull-in does not occur.

(3) A wavefront aberration compensating apparatus according to (1) or (2), wherein the wavefront sensor comprises: a Hartmann plate in which micro-lenses are aligned in a lattice-like configuration; and a two-dimensional charge-coupled device, and wherein the wavefront sensor measures the wavefront aberration of the object by: dividing light reflected from the object according to projection of a point light source onto the object and traveled through the object and the deformable mirror into plural light fluxes by the Hartmann plate; measuring point-image positions of the respective light fluxes by the two-dimensional charge-coupled device; and comparing the measured point-image positions with point-image positions according to an ideal object in which the aberration compensation is unnecessary.

Therefore, it is possible to satisfy the demand for high accuracy in the measurement of the wavefront aberration essential when the compensation of the higher order wavefront aberration at high accuracy is to be performed.

(4) A wavefront aberration compensating apparatus according to any one of (1) to (3), wherein the memory stores therein the voltage template provided for each of the expansion modes according to Zernike polynomials of the wavefront aberration, as the voltage alignment data for the electrodes which induces the corresponding expansion mode of the expansion modes subjected to the compensation.

Therefore, each of the expansion modes expanded by the Zernike polynomials corresponds to an independent shape or configuration of wavefront (mode). Hence, by compensating the wavefront aberration by using the voltage templates subsequently from a lower order of the respective expansion modes, it is possible to effectively converge the residual aberration to the target value.

(5) A wavefront aberration compensating apparatus according to any one of (1) to (4), wherein the controller is configured to: load an amplitude value in each of the expansion modes from expansion data according to Zernike polynomials of a residual aberration which is after the compensation of the wavefront aberration; load the voltage value applied to each of the electrodes as a previous voltage value used in a previous compensation of the wavefront aberration; load the stored voltage templates inducing the corresponding expansion modes; calculate objective Zernike polynomial data of the deformable mirror; load previously calculated a line-column in which wavefront configuration data corresponding to the respective voltage templates are aligned; calculate a superposition coefficient obtained from the calculated objective Zernike polynomial data and the loaded line-column as the superposition amplitude value of each of the expansion modes; and calculate the voltage value applied to each of the electrodes in a current compensation, by the voltage templates, the calculated superposition coefficient as the superposition amplitude value, the previous voltage value, and a feedback gain.

Therefore, the influence of the imperfection of the templates, by which the expansion modes other than the single expansion mode which should be generated in each of the Zernike expansion modes are mixed is corrected. Hence, it is possible to perform the compensation of the higher order wavefront aberration at high accuracy, in which the influence by the other expansion modes is eliminated.

(6) A wavefront aberration compensating apparatus according to any one of (1) to (4), wherein the controller is configured to: load an amplitude value in each of the expansion modes from expansion data according to Zernike polynomials of a residual aberration which is after the compensation of the wavefront aberration; load the voltage value applied to each of the electrodes as a previous voltage value used in a previous compensation of the wavefront aberration; load the stored voltage templates inducing the corresponding expansion modes; calculate a ratio of wavefront configuration data corresponding to the respective voltage templates to wavefront configuration data of the respective expansion modes as the superposition amplitude value of each of the expansion modes; and calculate the voltage value applied to each of the electrodes, by the voltage templates, the calculated ratio as the superposition amplitude value, the previous voltage value, and a feedback gain.

Therefore, it is possible to perform the compensation of the higher order wavefront aberration by increasing the speed of the calculation processing, while the accuracy of eliminating the influence by the main component of the templates with respect to the wavefront configuration data, within the influence of the imperfection of the templates by which the expansion modes other than the single expansion mode which should be generated in each of the Zernike expansion modes are mixed, is maintained.

(7) A wavefront aberration compensating apparatus according to any one of (1) to (4), wherein the controller is configured to: load an amplitude value in each of the expansion modes from expansion data according to Zernike polynomials of a residual aberration which is after the compensation of the wavefront aberration; load the voltage value applied to each of the electrodes as a previous voltage value used in a previous compensation of the wavefront aberration; load the stored voltage templates inducing the corresponding expansion modes; calculate a value obtained by reversing plus and minus signs of the amplitude value in each of the expansion modes as the superposition amplitude value of each of the expansion modes; and calculate the voltage value applied to each of the electrodes, by the voltage templates, the calculated value as the superposition amplitude value, the previous voltage value, and a feedback gain.

Therefore, it is possible to perform the compensation of the higher order wavefront aberration by increasing the speed of the calculation processing significantly, by normalizing the templates.

(8) A wavefront aberration compensating apparatus according to any one of (1) to (7), wherein the controller is configured to repeat the compensation of the configuration of the thin-film mirror of the deformable mirror, until a residual aberration after the compensation of the wavefront aberration becomes equal to or less than a target value determined on the basis of an allowable wavefront aberration in which a sharp image at the time when at least one of observation and photographing of the object is obtained by a set magnification.

Therefore, it is possible to obtain a sharp image when observing and photographing for example of an object subjected to the compensation of the aberration, regardless of magnitude of set magnification.

(9) A wavefront aberration compensating apparatus according to any one of (1) to (8), wherein the object comprises an eye, and wherein the controller is configured to: perform compensation of a spherical diopter power component and an astigmatism power component within the wavefront aberration generated due to a flexing characteristic of the eye as a lower order wavefront aberration compensation; and compensate a component of the wavefront aberration remained after the lower order wavefront aberration compensation and a component of the wavefront aberration higher in order than orders subjected to the lower order wavefront aberration compensation by deforming the deformable mirror.

Therefore, it is possible to reduce the burden in the compensation for the higher order wavefront aberration performed by deforming the deformable mirror, in the ophthalmologic unit in which the eye is set as the object subjected to the aberration compensation.

(10) A wavefront aberration compensating apparatus according to (9), wherein the controller is configured to: adjust the spherical diopter power component within the wavefront aberration by a focusing mechanism of an autofocusing system, on the basis of the measurement of the wavefront aberration by the wavefront sensor; adjust the astigmatism power component within the wavefront aberration by a lens for astigmatism compensation, on the basis of the measurement of the wavefront aberration by the wavefront sensor; and repeat the lower order wavefront aberration compensation by the adjustment of the spherical diopter power component with the focusing mechanism and the adjustment of the astigmatism power component with the lens, until a residual aberration after the compensation of the wavefront aberration becomes equal to or less than a defined value determined on the basis of second order in the expansion modes according to Zernike polynomials.

Therefore, it is possible to negate the astigmatism power component and the spherical diopter power component as the lower order wavefront aberration at a short time, by utilizing lenses provided in an optical path.

(11) A wavefront aberration compensating apparatus according to (9) or (10), wherein the controller is configured to: initiate the compensation of the configuration of the thin-film mirror of the deformable mirror after the lower order wavefront aberration compensation is performed; and repeat the compensation of the configuration of the thin-film mirror of the deformable mirror, until the residual aberration after the compensation of the wavefront aberration becomes equal to or less than a target value determined on the basis of the orders in the expansion modes by the Zernike polynomials, at least to the sixth order.

Therefore, the residual aberration to the 6th order is removed by the compensation for the higher order wavefront aberration performed by deforming the deformable mirror, in the ophthalmologic unit in which the eye is set as the object subjected to the aberration compensation. Hence, it is possible to obtain the sharp image of, for example, the retina at high magnification by which the observation to the degree of the visual cell is possible. In addition, it is possible to satisfy the demand for the higher magnification, by determining the target value in consideration of the orders from the 6th to 10th in the expansion modes according to the Zernike polynomials.

(12) A wavefront aberration compensating apparatus according to any one of (1) to (11), wherein the controller is configured to perform at least one of observation and photographing of a retina of an eye as the object, when a residual aberration after the wavefront aberration becomes equal to or less than a target value.

Therefore, it is possible to suppress the wavefront aberration to be small in a short time even when, for example, the eye as a cause of the generation of the wavefront aberration is set in an optical system, and to perform the observation, the photographing and so on of the retina of the eye with the sharp image at the high magnification.

(13) An ophthalmologic unit, comprising the wavefront aberration compensating apparatus according to any one of (1) to (12).

Therefore, it is possible to provide the ophthalmologic unit which suppress the residual aberration to be small with good responsiveness at the short time, and which obtains the extremely sharp image even if the high-magnification is set, even when the deformable mirror having the large number of electrodes to which the corresponding voltage is applied to each of those, is used for the compensation of the wavefront aberration.

(14) A wavefront aberration compensating apparatus, comprising: a deformable mirror which compensates a wavefront aberration of a light flux entered, the deformable mirror including a plurality of electrodes, and a thin-film mirror which changes a configuration thereof in accordance with a voltage value applied to each of the electrodes; an optical system provided with the deformable mirror, and including an object subjected to aberration compensation; a wavefront sensor which receives the light flux traveled through the object and the deformable mirror, and which measures the wavefront aberration of the light flux; voltage template storing means for storing therein a voltage template provided for each expansion mode according to a polynomial of wavefront aberration, as a voltage alignment data for the electrodes which induces the corresponding expansion mode of the expansion modes; voltage calculating means for determining a superposition amplitude value of each of the expansion modes, and calculating the voltage value applied to each of the electrodes by using the voltage templates stored in the voltage template storing means, such that the wavefront aberration obtained by the wavefront sensor becomes a desired aberration; and deformable mirror controlling means for performing a control of repeating compensation of the configuration of the thin-film mirror of the deformable mirror on the basis of the voltage value calculated by the voltage calculating means, such that the wavefront aberration of the light flux measured by the wavefront sensor is suppressed.

Therefore, it is possible to suppress the residual aberration to be small with good responsiveness at the short time, and to obtain the extremely sharp image even if the high-magnification is set, even when the deformable mirror having the large number of electrodes to which the corresponding voltage is applied to each of those, is used for the compensation of the wavefront aberration.

Although the present invention has been described in terms of exemplary embodiments, it is not limited thereto. It should be appreciated that variations may be made in the embodiments described by persons skilled in the art without departing from the scope of the present invention as defined by the following claims. The limitations in the claims are to be interpreted broadly based on the language employed in the claims and not limited to examples described in the present specification or during the prosecution of the application, and the examples are to be construed as non-exclusive. For example, in the present disclosure, the term "preferably", "preferred" or the like is non-exclusive and means "preferably", but not limited to. The use of the terms first, second, etc. do not denote any order or importance, but rather the terms first, second, etc. are used to distinguish one element from another. Moreover, no element or component in the present disclosure is intended to be dedicated to the public regardless of whether the element or component is explicitly recited in the following claims.

What is claimed is:

1. A wavefront aberration compensating apparatus, comprising:
    a deformable mirror which compensates a wavefront aberration of a light flux entered, the deformable mirror including a plurality of electrodes, and a thin-film mirror which changes a configuration thereof in accordance with a voltage value applied to each of the electrodes;
    an optical system provided with the deformable mirror, and including an object subjected to aberration compensation;
    a wavefront sensor which receives the light flux traveled through the object and the deformable mirror, and which measures the wavefront aberration of the light flux;
    a memory which stores therein a voltage template provided for each expansion mode according to a polynomial of wavefront aberration, as a voltage alignment data for the electrodes which induces the corresponding expansion mode of the expansion modes; and
    a controller configured to determine a superposition amplitude value of each of the expansion modes and calculate the voltage value applied to each of the electrodes by using the voltage templates stored in the memory, such that the wavefront aberration obtained by the wavefront sensor becomes a desired aberration, and to repeat compensation of the configuration of the thin-film mirror of the deformable mirror on the basis of the calculated voltage value, such that the wavefront aberration of the light flux measured by the wavefront sensor is suppressed.

2. A wavefront aberration compensating apparatus according to claim 1, wherein the controller is configured to:
    apply an initial voltage to each of the electrodes such that an displacement amount of the thin-film mirror becomes an initial displacement amount; and
    control the configuration of the thin-film mirror created according to a voltage pattern generated for the electrodes to be a configuration which negates a configuration of the wavefront aberration of the light flux entered through the object, such that the wavefront aberration included in the light flux after reflection from the deformable mirror is suppressed to be small.

3. A wavefront aberration compensating apparatus according to claim 1, wherein the wavefront sensor comprises:

a Hartmann plate in which micro-lenses are aligned in a lattice-like configuration; and a two-dimensional charge-coupled device, and wherein the wavefront sensor measures the wavefront aberration of the object by:

dividing light reflected from the object according to projection of a point light source onto the object and traveled through the object and the deformable mirror into plural light fluxes by the Hartmann plate;

measuring point-image positions of the respective light fluxes by the two-dimensional charge-coupled device; and comparing the measured point-image positions with point-image positions according to an ideal object in which the aberration compensation is unnecessary.

4. A wavefront aberration compensating apparatus according to claim 1, wherein the memory stores therein the voltage template provided for each of the expansion modes according to Zernike polynomials of the wavefront aberration, as the voltage alignment data for the electrodes which induces the corresponding expansion mode of the expansion modes subjected to the compensation.

5. A wavefront aberration compensating apparatus according to claim 1, wherein the controller is configured to:

load an amplitude value in each of the expansion modes from expansion data according to Zernike polynomials of a residual aberration which is after the compensation of the wavefront aberration;

load the voltage value applied to each of the electrodes as a previous voltage value used in a previous compensation of the wavefront aberration;

load the stored voltage templates inducing the corresponding expansion modes;

calculate objective Zernike polynomial data of the deformable mirror;

load previously calculated a line-column in which wavefront configuration data corresponding to the respective voltage templates are aligned;

calculate a superposition coefficient obtained from the calculated objective Zernike polynomial data and the loaded line-column as the superposition amplitude value of each of the expansion modes; and calculate the voltage value applied to each of the electrodes in a current compensation, by the voltage templates, the calculated superposition coefficient as the superposition amplitude value, the previous voltage value, and a feedback gain.

6. A wavefront aberration compensating apparatus according to claim 1, wherein the controller is configured to:

load an amplitude value in each of the expansion modes from expansion data according to Zernike polynomials of a residual aberration which is after the compensation of the wavefront aberration;

load the voltage value applied to each of the electrodes as a previous voltage value used in a previous compensation of the wavefront aberration;

load the stored voltage templates inducing the corresponding expansion modes;

calculate a ratio of wavefront configuration data corresponding to the respective voltage templates to wavefront configuration data of the respective expansion modes as the superposition amplitude value of each of the expansion modes; and calculate the voltage value applied to each of the electrodes, by the voltage templates, the calculated ratio as the superposition amplitude value, the previous voltage value, and a feedback gain.

7. A wavefront aberration compensating apparatus according to claim 1, wherein the controller is configured to:

load an amplitude value in each of the expansion modes from expansion data according to Zernike polynomials of a residual aberration which is after the compensation of the wavefront aberration;

load the voltage value applied to each of the electrodes as a previous voltage value used in a previous compensation of the wavefront aberration;

load the stored voltage templates inducing the corresponding expansion modes;

calculate a value obtained by reversing plus and minus signs of the amplitude value in each of the expansion modes as the superposition amplitude value of each of the expansion modes; and calculate the voltage value applied to each of the electrodes, by the voltage templates, the calculated value as the superposition amplitude value, the previous voltage value, and a feedback gain.

8. A wavefront aberration compensating apparatus according to claim 1, wherein the controller is configured to repeat the compensation of the configuration of the thin-film mirror of the deformable mirror, until a residual aberration after the compensation of the wavefront aberration becomes equal to or less than a target value determined on the basis of an allowable wavefront aberration in which a sharp image at the time when at least one of observation and photographing of the object is obtained by a set magnification.

9. A wavefront aberration compensating apparatus according to claim 1, wherein the object comprises an eye, and wherein the controller is configured to:

perform compensation of a spherical diopter power component and an astigmatism power component within the wavefront aberration generated due to a flexing characteristic of the eye as a lower order wavefront aberration compensation; and compensate a component of the wavefront aberration remained after the lower order wavefront aberration compensation and a component of the wavefront aberration higher in order than orders subjected to the lower order wavefront aberration compensation by deforming the deformable mirror.

10. A wavefront aberration compensating apparatus according to claim 9, wherein the controller is configured to:

adjust the spherical diopter power component within the wavefront aberration by a focusing mechanism of an autofocusing system, on the basis of the measurement of the wavefront aberration by the wavefront sensor;

adjust the astigmatism power component within the wavefront aberration by a lens for astigmatism compensation, on the basis of the measurement of the wavefront aberration by the wavefront sensor; and repeat the lower order wavefront aberration compensation by the adjustment of the spherical diopter power component with the focusing mechanism and the adjustment of the astigmatism power component with the lens, until a residual aberration after the compensation of the wavefront aberration becomes equal to or less than a defined value determined on the basis of second order in the expansion modes according to Zernike polynomials.

11. A wavefront aberration compensating apparatus according to claim 10, wherein the controller is configured to:

initiate the compensation of the configuration of the thin-film mirror of the deformable mirror after the lower order wavefront aberration compensation is performed; and repeat the compensation of the configuration of the thin-film mirror of the deformable mirror, until the residual aberration after the compensation of the wavefront aberration becomes equal to or less than a target value determined on the basis of the orders in the expansion modes by the Zernike polynomials, at least to the sixth order.

12. A wavefront aberration compensating apparatus according to claim 9, wherein the controller is configured to:
   initiate the compensation of the configuration of the thin-film mirror of the deformable mirror after the lower order wavefront aberration compensation is performed; and
   repeat the compensation of the configuration of the thin-film mirror of the deformable mirror, until a residual aberration after the compensation of the wavefront aberration becomes equal to or less than a target value determined on the basis of orders in the expansion modes by Zernike polynomials, at least to the sixth order.

13. A wavefront aberration compensating apparatus according to claim 1, wherein the controller is configured to perform at least one of observation and photographing of a retina of an eye as the object, when a residual aberration after the wavefront aberration becomes equal to or less than a target value.

14. An ophthalmologic unit, comprising the wavefront aberration compensating apparatus according to claim 13.

15. A wavefront aberration compensating apparatus, comprising:
   a deformable mirror which compensates a wavefront aberration of a light flux entered, the deformable mirror including a plurality of electrodes, and a thin-film mirror which changes a configuration thereof in accordance with a voltage value applied to each of the electrodes;
   an optical system provided with the deformable mirror, and including an object subjected to aberration compensation;
   a wavefront sensor which receives the light flux traveled through the object and the deformable mirror, and which measures the wavefront aberration of the light flux;
   voltage template storing means for storing therein a voltage template provided for each expansion mode according to a polynomial of wavefront aberration, as a voltage alignment data for the electrodes which induces the corresponding expansion mode of the expansion modes;
   voltage calculating means for determining a superposition amplitude value of each of the expansion modes, and calculating the voltage value applied to each of the electrodes by using the voltage templates stored in the voltage template storing means, such that the wavefront aberration obtained by the wavefront sensor becomes a desired aberration; and
   deformable mirror controlling means for performing a control of repeating compensation of the configuration of the thin-film mirror of the deformable mirror on the basis of the voltage value calculated by the voltage calculating means, such that the wavefront aberration of the light flux measured by the wavefront sensor is suppressed.

* * * * *